United States Patent [19]

Fischer et al.

[11] Patent Number: 5,391,749
[45] Date of Patent: * Feb. 21, 1995

[54] SUBSTITUTED NAPHTHACENE-5,12-DIONES AND THEIR USE

[75] Inventors: Walter Fischer, Reinach; Marcus Baumann, Basle, both of Switzerland; Jürgen Finter, Freiburg, Germany; Vratislav Kvita, Reinach; Carl W. Mayer, Riehen, both of Switzerland; Wolfgang Wernet, Freiburg, Germany

[73] Assignee: Ciba-Geigy Corporation, Ardsley, N.Y.

[*] Notice: The portion of the term of this patent subsequent to May 12, 2009 has been disclaimed.

[21] Appl. No.: 843,656

[22] Filed: Feb. 28, 1992

Related U.S. Application Data

[62] Division of Ser. No. 356,830, May 24, 1989, Pat. No. 5,112,977.

[30] Foreign Application Priority Data

May 27, 1988 [CH] Switzerland ............... 2008/88
Jul. 19, 1988 [CH] Switzerland ............... 2757/88

[51] Int. Cl.$^6$ .................................. C07D 211/06
[52] U.S. Cl. ................................ 546/195; 548/406; 552/201; 522/48
[58] Field of Search ................ 552/201; 522/48; 546/195; 548/406

[56] References Cited

U.S. PATENT DOCUMENTS

| | | | |
|---|---|---|---|
| 3,787,212 | 1/1974 | Heimsch | 522/48 |
| 4,046,577 | 9/1977 | Muzyczko | 522/68 |
| 4,309,413 | 8/1977 | Kraemer | 522/86 |
| 4,617,151 | 10/1986 | Mayer et al. | 540/1 |
| 4,661,595 | 4/1987 | Avar | 522/53 |
| 4,801,701 | 1/1989 | Hilti et al. | 540/1 |
| 5,001,243 | 3/1991 | Fischer | 552/201 |
| 5,112,977 | 5/1992 | Fischer | 552/201 |

FOREIGN PATENT DOCUMENTS 109360 5/1984 European Pat. Off. .
195743 9/1986 European Pat. Off. .

OTHER PUBLICATIONS

Chem. Abst. vol. 91 (1979) 74384d.
Tetrahedron Letters vol. 25 No. 42 pp. 4833–4836 (1984) Warrener et al.
Journal of the American Chem. Soc. (1973) pp. 4606–4610 Zimmerman et al.
Bulletin Del La Societe Chimique De framse 1973 pp. 1154–1159.
Chem. Abst. vol. 76 (1972) 73712n.
Annalen Der Chemie vol. 754 (1971) pp. 64–89.
(List continued on next page.)

Primary Examiner—Marion E. McCamish
Assistant Examiner—Mark A. Chapman
Attorney, Agent, or Firm—Kevin T. Mansfield; George R. Dohmann

[57] ABSTRACT

Substituted naphthacenediones of the formula I in which $R^1$ to $R^8$ are H and at least one of $R^1$ to $R^8$, for example $R^2$ and $R^3$ or $R^2$ and $R^6$, are, for example, $C_1$–$C_{20}$alkoxy, $C_1$–$C_{20}$alkenoxy, $C_1$–$C_{20}$-alkylsulfinyl, —CN, —CF$_3$, —NO$_2$, —Si(CH$_3$)$_3$ or —COO($C_1$–$C_{12}$alkyl), are suitable, when incorporated into polymers having hydroxyalkyl groups, for currentless deposition of metals onto the polymer surface. They are in some cases suitable as photoinitiators.

10 Claims, No Drawings

OTHER PUBLICATIONS

Chem. Abst. vol. 74 (1971) 93441k.

Tetrahedron vol. 26 pp. 5465–5478.

General Biochem. vol. 84 1976, p. 133 Abstract #106796b.

Laduranty et al. Can. J. Chem. vol. 58 pp. 1161–1167 (1980).

Bee et al. J. Chem. Research pp. 4301–4308 (1981).

Freemanis et al. Chem. Abst. vol. 86 item 189773v (1977) p. 597.

Derwent Abst. of JA 9081–440 (1974).

Smith J. Chem. Soc. pp. 673–674 (1962).

Farina et al. Cin. Quin., Ser. C vol. 81 (2) pp. 133–138 (1985).

McOmh et al. Synthesis p. 416 (1973).

Chemical Abstracts, 11th Collective Index (vol. 96–105) Chemical Substances pp. 41661cs, (1982–86).

SUBSTITUTED NAPHTHACENE-5,12-DIONES AND THEIR USE

This is a divisional of Ser. No. 356,830, filed May 24, 1989, now U.S. Pat. No. 5,112,977.

The present invention relates to substituted naphthacene-5,12-diones and their use as photoinitiators or sensitizers for the photopolymerization of compounds having at least one polymerizable or dimerizable ethylenically unsaturated double bond, or for currentless deposition of metal onto the surface of polymers containing hydroxyalkyl groups.

Only few substituted naphthacene-5,12-diones have been disclosed to date. They are useful intermediates for the preparation of tetrachalcogenated tetracenes. Such tetrachalcogenated tetracenes form electrically conductive charge transfer complexes with electron donors. 2- and 2,3-carboxylic acids and carboxylic acid derivatives of naphthacene-5,12-dione are described, for example, in U.S. Pat. No. 4,617,151. 2,7- and 2,8-difluoronaphthacene-5,12-dione are mentioned in DE-OS 3,635,124.

1-Hydroxyl- and 1-amino-naphthacene-5,12-diones which are substituted in the 4-position and optionally in the 3-position are described as flurescent disperse dyestuffs in Japanese Patent Publication 49-81440. In Annales die Quimica, Ser. C. 81(2), pages 133–138 (1982), F. F. y T. Torres describes the preparation of 2-hydroxy-, 2-methoxy-, 2-ethoxy- and 2-(2-hydroxyethoxy)naphthacene-5,12-dione. Naphthacene-5,12-diones having methoxy groups in the 6-, 7-, 8- and 9-positions are described, for example, in D. C. C. Smith, J. Chem. Soc., page 673 (1962), J. F. W. McOmie et al., Synthesis, page 416 (1973), and J. Laduranty et al., Can. J. Chem., volume 58, page 1161 (1980). 7-Methyl-naphthacene-5,12-dione is described by L. K. Bee et al. in J. Chem. Res. (M), page 4301 (1981). 2-Isopropyl-naphthacene-5,12-dione is mentioned in CA 86, 189773u (1977).

The present invention relates to compounds of the formula I

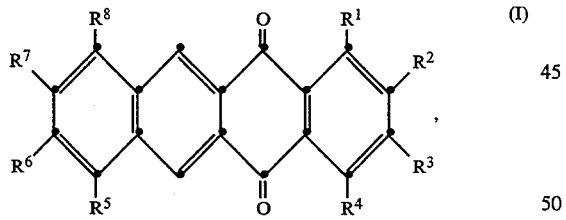

wherein a) $R^1$, $R^2$ $R^3$ and $R^4$ are H and $R^5$ to $R^8$ are each H and at least one of the radicals $R^5$ to $R^8$, independently of one another, is a substituent from the group comprising $C_1$-$C_{20}$alkyl-$X$$-_p$, with the exception of methyl and methoxy, $C_2$-$C_{18}$alkenyl-$(X)-_p$, $C_2$-$C_{18}$alkynyl-$X-_p$, $C_3$-$C_8$cycloalkyl-$(X)-_p$, ($C_1$-$C_{12}$alkyl)-$C_3$-$C_8$cycloalkyl-$(X)-_p$, $C_3$-$C_8$-cycloalkyl-$C_rH_{2r}$-$X-_p$, ($C_1$-$C_{12}$alkyl)-$C_3$-$C_8$cycloalkyl-$C_rH_{2r}$-$X-_p$, phenyl-$X-_p$, ($C_1$-$C_{12}$alkyl)phenyl-$(X-_p$, phenyl-$C_rH_{2r}$-$(X)-_p$ and ($C_1$-$C_{12}$alkyl)phenyl-$C_rH_{2r}$-$(X)-_p$ which are unsubstituted or substituted by halogen, —CN, furfuryl, —$NR^9R^{10}$, —$OR^9$, —$SR^9$ or $COOR^9$, r is 1 or 2, p is 0 or 1 and X is —O—, —SO— or —$SO_2$—, or $R^5$ to $R^8$ independently are a substituent from the group comprising halogen, —$NO_2$, —$CF_3$, —CN, —$NR^9R^{10}$, —$COOR^9$ —$CONR^9R^{10}$, —COCl, —SH, —Si($C_1$-$C_4$alkyl)$_3$ and —O$-(-C_mH_{2m}$—O$-)-_nR^{11}$, or in each case two adjacent radicals from $R^5$ to $R^8$ together are —CO—O—CO— or —CO—$NR^9$—CO—, $R^9$ and $R^{10}$ independently of one another are H, $C_1$-$C_{12}$alkyl, phenyl or —$C_mH_{2m}$—O$-)-_qR^{11}$, or $R^9$ and $R^{10}$ together are tetramethylene, pentamethylene, 3-oxapentylene or —$CH_2CH_2NR^9CH_2CH_2$—, $R^{11}$ is H or $C_1$-$C_{12}$-alkyl, m is a number from 2 to 4, n is a number from 2 to 20 and q is a number from 1 to 20, or b) $R^1$ to $R^8$ independently of one another are H or one of the substituents defined above, including methyl and methoxy, wherein $R^1$, $R^4$, $R^5$ and $R^8$ are also substituents with X in the meaning of —S— and at least one of $R^1$ to $R^4$ and $R^5$ to $R^8$ is a substituent, with the exception of $R^2$ and $R^6$ or $R^7$ as —F, or c) $R^5$ to $R^8$ are H, at least one of $R^1$, $R^2$, $R^3$ and $R^4$ is a substituent and $R^1$ and $R^4$ independently of one another are H or a substituent from the group comprising —$NO_2$, —$CF_3$, —CN, —$COOR^9$, —$CONR^9R^{10}$ —COCl, —Si($C_1$-$C_4$-alkyl)$_3$, —S$-(-C_mH_{2m}$—O$-)-_nR^{11}$ and —O$-(-C_mH_{2m}$—O$-)-_nR^{11}$, and $C_1$-$C_{20}$alkyl-$X$—, where X is —SO— or —$SO_2$, which is unsubstituted or substituted as defined under a); $C_2$-$C_{18}$alkenyl-$(X)-_p$, $C_2$-$C_{18}$alkynyl-$(X-_p$, $C_3$-$C_8$cycloalkyl-$X-_p$, ($C_1$-$C_{12}$alkyl)$C_3$-$C_8$cycloalkyl-$(X)-_p$, $C_3$-$C_8$cycloalkyl-$C_rH_{2r}$-$(X)-_p$ and ($C_1$-$C_{12}$alkyl)-$C_3$-$C_8$cycloalkyl-$C_rH_{2r}$-$(X)-_p$; phenyl-$(X)-_p$ and ($C_1$-$C_{12}$alkyl)-phenyl-$(X)-_p$, where X is —SO— or —$SO_2$—; phenyl-$C_rH_{2r}$-$(X)-_p$ and ($C_1$-$C_{12}$alkyl)-phenyl-$C_rH_{2r}$-$X-_p$; and $C_1$-$C_{20}$alkylthio which is substituted as defined above under a), phenyloxy, ($C_1$-$C_{12}$alkyl)phenyloxy and $C_1$-$C_{20}$alkoxy which is substituted by halogen, —CN, —$NR^9R^{10}$, —$SR^9$, —$OR^9$ or COOR; wherein $R^1$ is not —COOH if $R^2$ $R^3$ and $R^4$ are H, and $R^2$ and $R^3$ independently of one another are H or a substituent from the group comprising $C_5$-$C_{20}$alkyl, $C_3$-$C_{20}$alkoxy and $C_1$-$C_2$-$_0$alkyl-$X$—, where X is —SO— or —$SO_2$—, which are unsubstituted or substituted as defined above under a); and phenyl-$X$—, ($C_1$-$C_{12}$alkyl)phenyl-$(X)-_p$, ($C_1$-$C_{12}$alkyl)phenyl-$C_rH_{2r}$-$(X)-_p$, phenyl-$C_rH_{2r}$-$(X)-_p$, $C_2$-$C_{20}$alkenyl-$(X)-_p$, $C_2$-$C_{20}$alkynyl-$(X)-_p$, $C_3$-$C_8$cycloalkyl-$(X)-_p$, ($C_1$-$C_{12}$alkyl)-$C_3$-$C_8$cycloalkyl-$(X)-_p$, $C_3$-$C_8$cycloalkyl-$C_rH_{2r}$-$(X)-_p$ or ($C_1$-$C_{12}$alkyl)-$C_3$-$C_8$cycloalkyl-$C_rH_{2r}$-$(X)-_p$, where X is —O—, —SO— or —$SO_2$; or one of $R^2$ and $R_3$ or $R^2$ and $R^3$ are a substituent from the group comprising phenyl which is substituted as defined above under a); or one of $R^2$ and $R^3$ or $R^2$ and $R^3$ are a substituent from the group comprising $C_1$-$C_4$alkyl and $C_1$-$C_2$alkoxy, which are substituted by halogen, —CN, —$NR^9R^{10}$, —$OR^9$ —$SR^9$ or —$COOR^9$, with the exception of 2-hydroxyethyl; or one of $R^2$ and $R^3$ or $R^2$ and $R^3$ are a substituent from the group comprising SH, —$NO_2$, —$CF_3$, —CN, —$NR^9R^{10}$, —Si($C_1$-$C_4$alkyl)$_3$ and —O$-(-C_mH_{2m}$—O$-)-_nR^{11}$, or one of $R^2$ and $R^3$ are halogen, —$COOR^9$, —$CONR^9R^{10}$ or COCl and the other of $R^2$ and $R^3$ is a substituent as defined under a), or the other of $R^2$ and $R^3$ is H, if at least one of $R^1$ and $R^4$ is one of the substituents defined above; or $R^2$ and $R^3$ together are —CO—O—CO— or —CO—$NR^9$—CO— and at least one of $R^1$ and $R^4$ are one of the substituents defined above, or $R_2$ and $R^3$ together independently of one another are $C_1$-$C_2$alkoxy, wherein $R^9$, $R^{10}$, $R^{11}$, X, m, n, p, q, r and s are as defined under a), unless characterized otherwise, or d) $R_5$ to $R^8$ are H and $R^1$ is unsubstituted $C_1$-$C_{20}$alkylthio, $C_1$-$C_{20}$alkoxy, phenyloxy, phenylthio, $C_1$-$C_{12}$alkylphenyloxy or $C_1$-$C_{12}$alkylphenylthio, or phenylthio or $C_1$-$C_{12}$alkylphenylthio which is substituted as defined under a).

In $C_1$-$C_{20}$alkyl$(X)_{-p}$ $R^1$ to $R^8$ in the context of the preceding definitions, the alkyl group can be linear or branched and can preferably contain 1 to 18, in particular 1 to 12 and especially 1 to 6 C atoms. Examples of alkyl groups are methyl, ethyl and the isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl and eicosyl. p is preferably 1.

In $C_2$-$C_{18}$alkenyl$(X)_{-p}$ $R^1$ to $R^8$ in the context of the preceding definitions, the alkenyl group can be linear or branched and can preferably contain 3 to 12, in particular 3 to 6, C atoms. The alkenyl preferably contains terminal double bonds. Some examples are ethenyl, allyl, prop-1-en-1- or -2-yl, but-1-en-1- or -2- or -3- or -4-yl, but-2-en-1- or -2-yl, pent-1-en- or pent-2-en-1- or -2- or -3- or -4- or -5-yl, hex-1-en- or hex-2-en- or hex-3-en-1- or -3- or -4- or -5-or -6-yl, heptenyl, octenyl, nonenyl, decenyl, undecyl, dodecenyl, tetracenyl, hexadecenyl and octadecenyl. p is preferably 1.

In $C_2$-$C_{18}$alkynyl$(X)_{-p}$ $R^1$ to $R^8$ in the context of the preceding definitions, the alkynyl group can be linear or branched and can preferably contain 3 to 12, in particular 3 to 6, C atoms. The triple bond is preferably in the terminal position. Some examples are ethynyl, propargyl, but-1-in-3- or -4-yl, but-2-in-1-yl, pent-1-in-3- or -4- or -5-yl, hex-1-in-3- or -4- or -5- or -6-yl, hex-2-in-1- or -4- or -5- or -6-yl, hex-3-in-1- or -2-yl, heptynyl, octynyl, nonynyl, decynyl, undecynyl and dodecyny, p is preferably 1.

$C_3$-$C_8$cycloalkyl$(X)_{-p}$ $R^1$ to $R^8$ in the context of the preceding definitions can be cyclopropyl, cyclobutyl, cyclopentyl, cyclohexyl, cycloheptyl or cyclooctyl. X is preferably —O—. $C_3$-$C_6$cycloalkyl is preferred. p is preferably 1.

In $C_3$-$C_8$cycloalkyl-$C_rH_{2r}(X)_{-p}$, ($C_1$-$C_{12}$alkyl)-$C_3$-$C_8$cycloalkyl$(X)_{-p}$ or ($C_1$-$C_{12}$alkyl)-$C_3$-$C_8$-cycloalkyl-$C_rH_{2r}(X)_{-p}$ $R^1$ to $R^8$ in the context of the preceding definitions, the alkyl group can be linear or branched and can preferably contain 1 to 6, in particular 1 to 4, C atoms. r in the —$C_rH_{2r}$— group is preferably 1. X is preferably —O—. In these substituents, the cycloalkyl group is preferably $C_3$-$C_6$cycloalkyl. p is preferably 1.

In ($C_1$-$C_{12}$alkyl)phenyl$(X)_{-p}$, phenyl-$C_rH_{2r}$—$(X)_{-p}$ or ($C_1$-$C_{12}$alkyl)phenyl$(X)_{-p}$ $R^1$ to $R^8$ in the context of the preceding definitions, the alkyl group can be linear or branched and can preferably contain 1 to 6, in particular 1 to 4, C atoms. r in the —$C_rH_{2r}$— group is preferably 1. p is preferably 1.

In the context of the preceding definitions, $R^1$ to $R^8$ can be unsubstituted or substituted by one or more, preferably one to three and in particular one or two substituents. If the substituent is halogen, this is preferably —F, —Cl or —Br. If the substituent is —NR$^9$R$^{10}$, $R^9$ and $R^{10}$ preferably independently of one another are H or $C_1$-$C_4$alkyl, and in particular methyl or ethyl. If the substituent is —OR$^9$, —SR$^9$ or —COOR$^9$, $R^9$ is preferably H, $C_1$-$C_4$alkyl or —O$(-C_mH_{2m}O-)_n$R$^{11}$, in which R$^{11}$ is H or $C_1$-$C_4$alkyl, m is 2 or 3 and n is 1 to 12.

Halogen $R^1$ to $R^8$ in the context of the preceding definitions is, in particular, —F, —Cl or —Br.

In —NR$^9$R$^{10}$ or —CONR$^9$R$^{10}$ $R^1$ to $R^8$ in the context of the preceding definitions, $R^9$ and $R^{10}$ independently of one another are preferably $C_1$-$C_6$alkyl, or $R^9$ and $R^{10}$ together are preferably tetra- or pentamethylene or 3-oxapentylene.

—Si($C_1$-$C_4$alkyl)$_3$ $R^1$ to $R^8$ in the context of the preceding definitions is preferably —Si($C_1$ or $C_2$alkyl)$_3$, and in particular trimethylsilyl.

In —O$(-C_mH_{2m}$—O$-)_n$R$^{11}$ $R^1$ to $R^8$ in the context of the preceding definitions, R$^{11}$ is preferably H or $C_1$-$C_4$alkyl, m is preferably 2 or 3 and n is preferably 1 to 12, in particular 1 to 6.

Adjacent radicals for the groups —CO—O—CO— and —CO—NR$^9$—CO— are, in particular, $R^2$ and $R^3$ and/or $R^6$ and $R^7$.

Alkyl $R^9$ and $R^{10}$ preferably contain 1 to 6, in particular 1 to 4, C atoms and are, in particular, methyl or ethyl. The alkyl can be linear or branched.

In the group —$(C_mH_{2m}$—O$-)_n$R$^{11}$ $R^9$ and $R^{10}$, m is preferably 2 or 3, n is 1 to 12, in particular 2 to 6, and R$^{11}$ is H or $C_1$-$C_4$alkyl.

In a preferred embodiment, $R^9$ and $R^{10}$ independently of one another are H, $C_1$-$C_4$alkyl or phenyl, or $R^9$ and $R^{10}$ together are tetramethylene, pentamethylene or 3-oxapentylene.

Preferred embodiments of compounds of the formula I are those in which a) $R^5$ or $R^8$, or $R^4$, $R^5$ or $R^8$, or $R^1$, $R^4$, $R^5$ or $R^8$ are H, or b) $R^2$ or $R^3$ or $R^2$ and $R^3$ are a substituent, or c) $R^1$, $R^2$ and $R^3$ or $R^1$ and $R^2$ or $R^1$ and $R^3$ are a substituent, or d) $R^2$ and $R^3$ or $R^2$ or $R^3$ are a substituent and $R^6$ or $R^7$ or $R^6$ and $R^7$ are a substituent, or e) $R^1$, $R^2$ and $R^3$ or $R^1$ and $R^2$ or $R^1$ and $R^3$ are a substituent and $R^4$, $R^5$ and $R^8$ are H and $R^6$ or $R^7$ or $R^6$ and $R^7$ are H or a substituent. Preferred compounds of the formula I are those in which $R^4$ is H, or in which p in the substituent is 1.

A preferred sub-group of compounds of the formula I comprises those in which $R^1$ to $R^4$ and $R^5$ and $R^8$ are H; at least one of the radicals $R^6$ or $R^7$ is a substituent from the group comprising $C_1$-$C_{18}$alkyl$(X)_{-p}$, phenyl$(X)_{-p}$, ($C_1$-$C_6$alkyl)-phenyl$(X)_{-p}$, benzyl$(X)_{-p}$ and ($C_1$-$C_6$alkyl)benzyl$(X)_{-p}$, which are unsubstituted or substituted by F, Cl, Br, —CN, —NR$^9$R$^{10}$, —OR$^9$, —SR$^9$ or —COOR$^9$; unsubstituted $C_3$-$C_{12}$alkenoxy and $C_3$-$C_6$alkynoxy, the alkene or alkine group of which is not bonded to the O atom; and —F, —Cl, —Br, —NO$_2$, —CF$_3$, —CN, —NR$^9$R$^{10}$, COOR$^9$, —CONR$^9$R$^{10}$, —Si(CH$_3$)$_3$ and —O—$C_2H_4$O$-)_n$R$^{11}$; R$^{11}$ is H or $C_1$-$C_4$alkyl; X is —O—, —SO— or —SO$_2$—, Y is —O—, p is 0 or 1 and n is 2 to 20, and in which R$^9$ and R$^{10}$ are each H or $C_1$-$C_6$alkyl, or R$^9$ and R$^{10}$ together are tetra- or pentamethylene, 3-oxapentylene or —CH$_2$CH$_2$N—($C_1$-$C_6$alkyl)CH$_2$CH$_2$.

Another preferred sub-group of compounds of the formula I comprises those in which $R^4$, $R^5$ and $R^8$ are H; at least one of the radicals $R^1$, $R^2$ and $R^3$ and at least one of the radicals $R^6$ and $R^7$ are a substituent from the group comprising $C_1$-$C_{18}$alkyl$(X)_{-p}$, including methyl and methoxy, phenyl$(X)_{-p}$, ($C_1$-$C_6$alkyl)phenyl$(X)_{-p}$, benzyl$(X)_{-p}$ and ($C_1$-$C_6$alkyl)benzyl$(X)_{-p}$, which are unsubstituted or substituted by F, Cl, Br, —CN, ONR$^9$R$^{10}$, —OR$^9$, —SR$^9$ or —COOR$^9$; unsubstituted $C_3$-$C_{12}$alkenoxy or $C_3$-$C_6$alkynoxy, the alkene or alkine group of which is not bonded to the O atom; and —F, —Cl, —Br, —NO$_2$, —CF$_3$, —CN, —NR$^9$R$^{10}$, —COOR$^9$, —CONR$^9$R$^{10}$, —Si(CH$_3$)$_3$ and O$+$C$_2$H$_4$O$+_n$R$^{11}$; R$^{11}$ is H or C$_1$-C$_4$alkyl; X is —O—, —SO— or —SO$_2$—, Y is —O—, p is 0 or 1 and n is 2 to 20; and R$^9$ and R$^{10}$ are each H or C$_1$-C$_6$alkyl, or R$^9$ and R$^{10}$ together are tetra- or pentamethylene, 3-oxapentylene or —CH$_2$CH$_2$N(C$_1$-C$_6$alkyl)CH$_2$CH$_2$—.

A preferred sub-group of compounds of the formula I also comprises those in which R$^5$ to R$^8$ are H; R$^1$ and R$^4$ independently of one another are H or a substituent from the group comprising —NO$_2$, —CF$_3$, —CN, —COOR$^9$, —CONR$^9$R$^{10}$, —Si(CH$_3$)$_3$, —S$+$C$_2$H$_4$—O$+_n$R$^{11}$ and —O$+$C$_2$H$_4$—O$+_n$R$^{11}$, in which R$^9$ and R$^{10}$ are each H or C$_1$-C$_6$alkyl, or R$^9$ and R$^{10}$ together are tetramethylene, pentamethylene or 3-oxapentylene; R$^2$ and R$^3$ independently of one another are H or a substituent from the group comprising C$_5$-C$_{18}$alkyl, C$_3$-C$_{18}$alkoxy, C$_1$-C$_{18}$alkyl-X—, where X is —SO— or —SO$_2$—, phenyl-X—, (C$_1$-C$_6$alkyl)phenyl-X—, benzyl$(X)-_p$ or (C$_1$-C$_6$alkyl)benzyl$(X)-_p$ where X is —O—, —SO— or —SO$_2$— and p is 0 or 1, which are unsubstituted or substituted by —F, —Cl, —Br, —CN, —NR$^9$R$^{10}$, —OR$^9$, —SR$^9$ or COOR$^9$, and unsubstituted C$_3$-C$_{12}$alkoxy and C$_3$-C$_{12}$alkynoxy, the alkane or alkine group of which is not bonded to the O atom; and C$_1$-C$_4$alkyl and C$_1$-C$_2$alkoxy which are substituted by —F, —Cl, —Br, —CN, —NR$^9$R$^{10}$, —SR$^9$ or —OR$^9$; and —F, —Cl, —Br, —NO$_2$, —CF$_3$, —CN, —NR$^9$R$^{10}$, —Si(CH$_3$)$_3$ and $+$OC$_2$H$_4$O$+_n$R$^{11}$, where R$^{11}$ is H or C$_1$-C$_4$alkyl; or one of R$^2$ and R$^3$ is —F, —Cl, —COOR$^9$ or —CONR$^9$R$^{10}$ and the other of R$^2$ and R$^3$ is a substituent as defined for R$^6$ in Claim 8, or the other of R$^2$ and R$^3$ is H, if R$^1$ is a substituent; or R$^2$ and R$^3$ are —COOR$^9$ or —CONR$^9$R$^{10}$, or together are —CO—O—CO— or —CO—NR$^9$—CO—, if R$^1$ is a substituent as defined above; or R$^2$ and R$^3$ independently are methoxy or ethoxy; or R$^9$ and R$^{10}$ are each H or C$_1$-C$_6$alkyl, or R$^9$ and R$^{10}$ together are tetramethylene, pentamethylene, 3-oxapentylene or —CH$_2$CH$_2$N(C$_1$-C$_6$alkyl)CH$_2$CH$_2$—, and n is 2 to 12.

Another preferred sub-group comprises those compounds of the formula I in which R$^5$ to R$^8$ are H and R$^1$ is unsubstituted C$_1$-C$_{12}$alkylthio, C$_1$-C$_{12}$alkoxy, phenyloxy, (C$_1$-C$_6$alkyl)phenyloxy or (C$_1$-C$_6$alkyl)phenylthio or phenylthio or (C$_1$-C$_6$alkyl)phenylthio which is substituted by —F, —Cl, —OH, C$_1$-C$_4$alkoxy or C$_1$-C$_4$alkylthio.

Substituted alkyl R$^2$ and R$^3$ are, in particular, C$_1$-C$_6$-, in particular C$_1$- or C$_2$-alkyl, which is substituted by —CN or —COO(C$_1$-C$_{12}$alkyl), or benzyl.

A particularly preferred sub-group comprises those compounds of the formula I in which R$^1$ is H, —NO$_2$, —CF$_3$ or —COO(C$_1$-C$_4$alkyl); R$^4$, R$^5$ and R$^8$ are H; R$^3$, R$^6$ and R$^7$ are H and R$^2$ is C$_3$ to C$_{18}$alkoxy, C$_3$-C$_{12}$hydroxyalkyl or C$_3$-C$_6$dihydroxyalkyl, C$_3$-C$_{12}$alkenoxy or C$_3$-C$_6$alkynoxy, in which the —O— atom is not bonded to the alkene or alkine group, or —O$+$CH$_2$CH$_2$—O$+_n$R$^{11}$ where n is 2 to 12 and R$^{11}$ is H or C$_1$-C$_6$alkyl; phenyloxy which is unsubstituted or substituted by —F, —Cl, C$_1$-C$_4$alkyl, C$_1$-C$_4$alkoxy or C$_1$-C$_4$alkylthio; —NR$^9$R$^{10}$, where R$^9$ and R$^{10}$ are C$_1$-C$_6$alkyl, or together are pentamethylene or 3-oxapentylene; C$_1$-C$_6$alkyl-SO—, C$_1$-C$_4$alkyl-SO$_2$—, phenyl-SO— or phenyl-SO$_2$—; C$_1$-C$_4$alkyl or benzyl which is substituted by —CN or —COO(C$_1$-C$_6$alkyl) or —CN or —CF$_3$; R$^2$ and R$^3$ independently of one another are C$_1$-C$_2$alkoxy or —(O—CH$_2$CH$_2$)$_2$OR$^{11}$, where R$^{11}$ is H or C$_1$-C$_6$alkyl and n is 2 to 12; or —F, —Cl or —Br, or are as defined above for R$^2$; and R$^5$ and R$^8$ are H, and R$^6$ and R$^7$ independently are H, —F, —Cl, —Br, —CN, —CF$_3$, —Si(CH$_3$)$_3$, —NO$_2$, C$_1$-C$_{12}$alkoxy or —COO(C$_1$-C$_6$alkyl), with the exception of R$^2$ and R$^6$ or R$^7$ as —F and R$^1$ R$^4$, R$^5$ and R$^2$ as H; or R$^1$ to R$^5$ and R$^8$ are H, R$^6$ or R$^7$ is H and R$^7$ or R$^6$ or R$^6$ and R$^7$ independently of one another are —F, —Cl, —Br, —CN, —NO$_2$, —CF$_3$, —Si(CH$_3$)$_3$, —NO$_2$, —COO(C$_1$-C$_4$alkyl) or C$_1$-C$_{12}$alkoxy.

The compounds of the formula I can be prepared by reacting, by a Friedel-Crafts reaction, a naphthalenedicarboxylic anhydride of the formula II

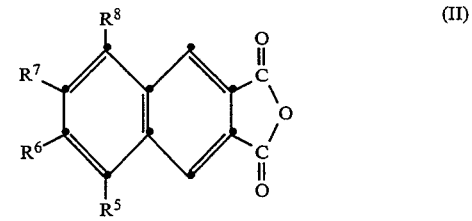

with a benzene of the formula III

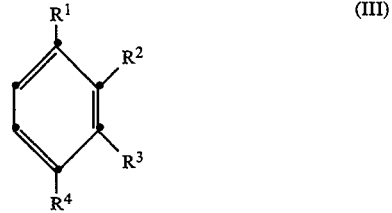

in which R$^1$ to R$^8$ are as defined above, in the presence of a Lewis acid, and if appropriate substituting compounds of the formula I in which at least one of R$^1$ to R$^8$ is —NO$_2$ or halogen with a nucleophilic compound. Halogen is preferably —Br, —Cl and, in particular, —F. Compounds which are suitable for the nucleophilic substitution are, in particular, those of the formula (R$^1$ to R$^8$)—X—H, in which X is —O—, —S—, —SO— or —SO$_2$, H—NR$^9$R$^{10}$, malonic acid esters or nitriles and phenylacetonitrile. The compounds can be used in the form of their alkali metal salts, for example Li, Na or K salts. It is also possible for the nucleophilic substitution to be carried out in the presence of bases, for example alkali metal hydroxide solutions or alkali metal carbonates.

The compounds of the formula I can also be prepared by reacting, in a Diols-Alder reaction, a compound of the formula IV

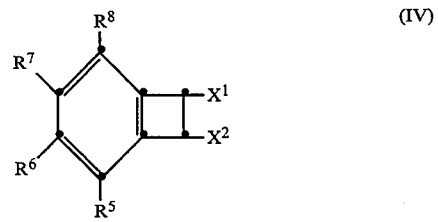

in which R$^5$, R$^6$, R$^7$ and R$^8$ are as defined above and X$^1$ and X$^2$ independently of one another are —Cl, —Br or —I, with a compound of the formula V

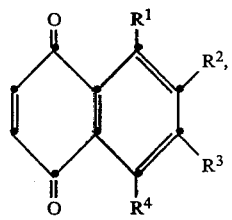
(V)

in which $R^1$, $R^2$, $R^3$ and $R^4$ are as defined above, $HX^1$ and $HX^2$ being split off. In the substituents $R^1$ to $R^8$, p is preferably 1.

The reaction is advantageously carried out at temperatures of 50° to 250° C., preferably 80° to 200° C. An inert solvent is advantageously used, for example polar aprotic solvents. Some examples are aromatic hydrocarbons (benzene, toluene, xylene, chlorobenzene and dichlorobenzene), nitriles (acetonitrile) and ethers (dibutyl ether, dioxane, tetrahydrofuran, ethylene glycol dimethyl ether and diethylene glycol dimethyl ether). The products can be isolated and purified by customary methods, for example crystallization, sublimation or chromatography.

Compounds of the formula IV are known in some cases (see, for example, H. P. Cava et al., J. Am. Chem. Soc., page 1701 (1957) and J. W. Barton et al., J. Chem. Soc. Perkin Trans. 1, pages 967–971 (1986)), or can be prepared by analogous processes. The substituted 1,2-bis(dichloro- or diboromomethyl)benzenes required for the preparation are likewise known in some cases or are obtainable by customary electrophilic or nucleophilic substitution reactions on corresponding o-dimethylbenzenes and subsequent chlorination or bromination of the products with, for example, N-chloro- or N-bromosuccinimide.

The 1,4-naphthoquinones of the formula V are known and are obtainable, for example, by nucleophilic substitution of halogeno- or nitro-1,4-naphthoquinones, which may be protected and substituted, with, for example, the compounds described above in the presence of alkali metal compounds, ($K_2CO_3$, $Cs_2CO_3$, KOH, NaOH, $NaNH_2$, $NaOCH_3$ or $NaOC_2H_5$), or with alkali metal compounds, for example of Li, K, Na, Rb, or Cs. Halogeno-and nitro-naphthoquinones are described, for example, in Houben-Weyl, Chinone I, (Quinones I), volume 7/3 b (1977). The naphthoquinones of the formula V can also be prepared in a known manner by electrophilic or nucleophilic substitution of unsubstituted or substituted naphthalenes or dihydro- or tetrahydronaphthalenes and subsequent conversion into the substituted 1,4-naphthoquinones.

Compounds of the formula I can also be prepared by reacting 1,2-bis(dihalogenomethyl)benzenes of the formula

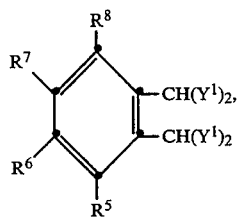

in which $Y^1$ is Cl, Br or I, with a compound of the formula V in the presence of NaI in an organic solvent.

This method is described by J. W. McOmie in Synthesis, pages 416–417 (1973).

Compounds of the formula I can also be obtained by reacting anthracene-1,4-quinones of the formula

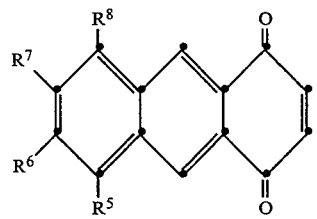

with an α-pyrone of the formula VI

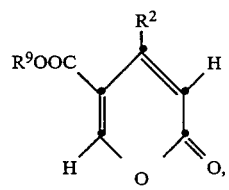
(VI)

or a butadiene of the formula VII

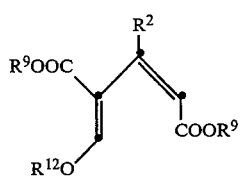
(VII)

in which $R^{11}$ is $C_1$–$C_6$alkyl and $R^9$ is as defined above, and is preferably $C_1$–$C_6$alkyl. This method and the preparation of α-pyrones is described in U.S. Pat. No. 4,617,151 and EP-A-0,195,743.

Compounds of the formulae VI and VII are obtainable, for example, as follows: In these formulae, $X^3$ is an alkali metal:

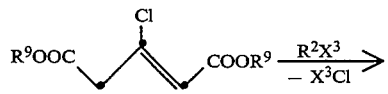

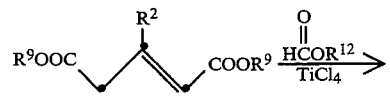

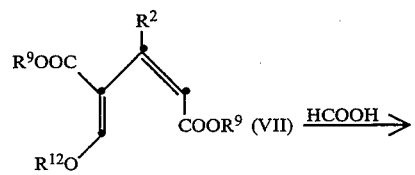

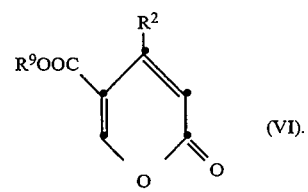
(VI).

If $R^1$ to $R^8$ are a polyoxaalkylene radical, such compounds are also obtained by reacting compounds of the formula I where $R^1$ to $R^8$ are hydroxyalkyl with epoxides. It is furthermore possible to convert the radicals $R^1$ to $R^8$ by classical reactions, for example hydrolysis, esterification or transesterification, amidation, oxidation or reduction. Carboxylic acid esters can be converted into the trifluoromethyl derivatives with $HF/SF_4$ in a known manner.

The compounds of the formula I are in general crystalline and are distinguished by a high heat stability. Compounds with oxy, sulfinyl or alkyl substituents can be dissolved very readily in curable compositions, if appropriate together with a solvent.

By themselves or together with H donors, for example tertiary amines or alcohols or phenylacetic acid derivatives, they are suitable as active photoinitiators or sensitizers for photo-induced polymerization or dimerization of ethylenically unsaturated compounds. In this application they are distinguished by a good photosensitivity and activity over a wavelength range from about 200 nm (UV light) to about 600 nm.

The properties of the compounds according to the invention, for example solubility, melting point and absorption range, can be influenced in a controlled manner by the choice of substituents.

The present invention furthermore relates to a composition which can be polymerized by radiation and contains (a) at least one non-volatile, monomeric, oligomeric or polymeric compound having at least one photopolymerizable or photodimerizable ethylenically unsaturated double bond and (b) at least one compound of the formula Ia as a photoinitiator or sensitizer,

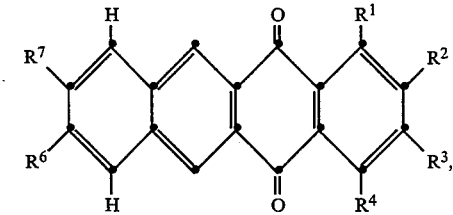

(Ia)

in which at least one of $R^1$ to $R^4$, $R^6$ and $R^7$ is a substituent, $R^1$ and $R^4$ independently of one another are H, $C_1$-$C_{18}$alkoxy or $-O+C_mH_{2m}-O+_nR^{11}$, where m is 2 to 4, n is 1 to 20 and $R^{11}$ is H or $C_1$-$C_{12}$alkyl, $R^2$, $R^3$, $R^6$ and $R^7$ independently of one another are H, $C_1$-$C_{18}$alkoxy, $C_1$-$C_{18}$alkyl—SO—, $-O+C_mH_{2m}-O+_nR^{11}$, $-COO(C_1$-$C_{18}$alkyl), $-COO+C_mH_{2m}-O+_nR^{11}$ or $C_1$-$C_6$alkyl, benzyl or $C_1$-$C_6$alkoxy which is substituted by 1 or 2 $-COO(C_1$-$C_{18}$alkyl) or $-COO+C_mH_{2m}-O+_nR^{11}$, wherein $R^{11}$, m and n are as defined above.

The compositions can contain further photoinitiators or sensitizers other than (b).

The amount of compounds according to the invention added essentially depends on economic aspects, on their solubilities and on the desired sensitivity. In general, 0.01 to 20, preferably 0.05–10 and in particular 0.1 to 5% by weight, based on component (a), is used.

Possible components (a) are those ethylenically unsaturated monomeric, oligomeric and polymeric compounds which react by photopolymerization to give higher molecular weight products and during this change their solubility.

Examples of particularly suitable compounds are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polybutadiene and butadiene copolymers, polyisoprene and isoprene copolymers, polymers and copolymers having (meth)acrylic groups in side chains, and mixtures of one or more such polymers.

Examples of unsaturated carboxylic acids are acrylic acid, methacrylic acid, crotonic acid, itaconic acid, cinnamic acid and unsaturated fatty acids, such as linolenic acid or oleic acid. Acrylic and methacrylic acid are preferred.

Aromatic and in particular aliphatic and cycloaliphatic polyols are suitable as the polyols. Examples of aromatic polyols are hydroquinone, 4,4'-dihydroxydiphenyl, 2,2-di(4-hydroxphenyl)-propane and novolaks and cresols. Examples of polyepoxides are those based on the polyols mentioned, in particular the aromatic polyols and epichlorohydrin. Polymers or copolymers containing hydroxyl groups in the polymer chain or in side groups, for example polyvinyl alcohol and copolymers thereof or polymethacrylic acid hydroxyalkyl esters or copolymers thereof, are furthermore also suitable as polyols. Other suitable polyols are oligoesters containing hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably 200 to 1500, 1,3-cyclopentanediol, 1,2-, 1,3- or 1,4-cyclohexanediol, 1,4-dihydroxymethylcyclohexane, glycerol, tris-($\beta$-hydroxyethyl)amine, trimethylolethane, trimethylolpropane, pentaerythritol, dipentaerythritol and sorbitol.

The polyols can be partly or completely esterified with one or different unsaturated carboxylic acids, it being possible for the free hydroxyl groups in partial esters to be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol trimethacrylate, tripentaerythritol octamethacrylate, pentaerrythritol diitaconate, dipentaerythritol triitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, modified pentaerythritol triacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol having a molecular weight of 200–1500, or mixtures thereof.

The amides of identical or different unsaturated carboxylic acids with aromatic, cycloaliphatic and aliphatic polyamines having preferably 2 to 6, in particular 2 to 4, amino groups are also suitable as component (a). Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine and di-(β-aminoethoxy)- or di(β-aminopropoxy)ethane. Other suitable polyamines are polymers and copolymers having amino groups in the side chain and oligoamides having amino end groups.

Examples of such unsaturated amides are: methylene-bis-acrylamide, 1,6-hexamethylene-bis-acrylamide, diethylenetriamine-tris-methacrylamide, bis(methacrylamidopropoxy)-ethane, β-methacrylamidoethyl methacrylate, N[(β-hydroxyethoxy)ethyl]-acrylamide.

Suitable unsaturated polyesters and polyamides are derived, for example, from maleic acid and diols or diamines. Some of the maleic acid can be replaced by other dicarboxylic acids. They can be used together with ethylenically unsaturated comonomers, for example styrene. The polyesters and polyamides can also be derived from dicarboxylic acids and ethylenically unsaturated diols or diamines, in particular from longer-chain compounds having, for example, 6 to 20 C atoms. Examples of polyurethanes are those which are built up from saturated or unsaturated diisocyanates and unsaturated or saturated diols.

Polybutadiene and polyisoprene and copolymers thereof are known. Examples of suitable comonomers are polyolefins, such as ethylene, propene, butene and hexene, (meth)acrylates, acrylonitrile, styrene or vinyl chloride. Polymers having (meth)acrylate groups in the side chain are likewise known. They can be, for example, reaction products of novolak-based epoxy resins with (meth)acrylic acid, homo- or copolymers of polyvinyl alcohol or hydroxyalkyl derivatives thereof esterified with (meth)acrylic acid, or homo- and copolymers of (meth)acrylates esterified with hydroxyalkyl (meth)acrylates.

The photopolymerizable compounds are employed by themselves or in any desired mixtures. Mixtures of polyol (meth)acrylates are preferably used.

Suitable dimerizable compounds are those which contain, for example, cinnamic acid radicals, dimethylmaleimidyl radicals

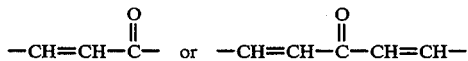

radicals. These radicals are in general bonded to oligomers or polymers, for example in the polymer chain or as side groups. Polymers having dimethylmaleimidyl groups are described, for example, in DE-A-2,626,795. Epoxy resins containing

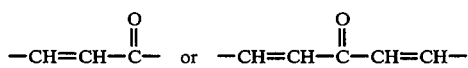

groups are described, for example, in DE-A-2,342,407.

Binders can also be added to the compositions according to the invention, and this is particularly advantageous if photopolymerizable or photodimerizable compounds are liquid or viscous substances. The amount of binder can be, for example, 5–95, preferably 10–90 and in particular 50–90% by weight, based on the entire composition. The binder is chosen according to the field of use and the properties required for this, such as developability in aqueous and organic solvent systems, adhesion to substrates and oxygen sensitivity.

Examples of suitable binders are polymers having a molecular weight of about 5000–2000000, preferably 10000 to 1000000. Examples are: homo- and copolymeric acrylates and methacrylates, for example copolymers of methyl methacrylate/ethyl acrylate/methacrylic acid, poly(methacrylic acid alkyl esters) and poly(acrylic acid alkyl esters); cellulose esters and ethers, such as cellulose acetate, cellulose acetobutyrate, methylcellulose and ethylcellulose; polyvinylbutyral, polyvinylformal, cyclized rubber and polyethers, such as polyethylene oxide, polypropylene oxide and polytetrahydrofuran; and polystyrene, polycarbonate, polyurethane, chlorinated polyolefins, polyvinyl chloride, copolymers of vinyl chloride/vinylidine chloride, copolymers of vinylidine chloride with acrylonitrile, methyl methacrylate and vinyl acetate, polyvinyl acetate, copoly(ethylene/vinyl acetate), polyamides, such as polycaprolactam and poly(hexamethyleneadipamide), and polyesters, such as poly(ethylene glycol terephthalate) and poly(hexamethylene glycol succinate).

The compositions according to the invention are suitable as coating agents for all types of substrates, for example wood, paper, ceramics, plastics, such as polyester and cellulose acetate films, and metals, such as copper and aluminum, onto which a protective layer or a photographic image is to be applied by photopolymerization. The present invention also relates to the coated substrates and a process for application of photographic images to the substrates. The coated substrates can also be used as recording material for holograms (volume phase diagram), it being advantageous that no wet development is necessary for this purpose.

The substrates can be coated by applying a liquid composition or a solution or suspension to the substrate. Liquid compositions without solvents are preferred.

The choice of solvent and the concentration depends chiefly on the nature of the composition and on the coating process. The composition is applied uniformly to a substrate by means of known coating processes, for example by dipping, knife-coating, curtain coating processes, electrophoresis, brushing on, spraying or reverse roll coating. The amount applied (coating thickness) and nature of the substrate (coating carrier) depend on the desired field of application. Examples of coating carriers which are used for photographic recording of information are films of polyester, cellulose acetate or paper coated with plastic; specially treated aluminum for offset printing plates and laminates coated with copper for the production of printed circuits. The coating thicknesses for photographic materials and offset printing plates are in general about 0.5 to about 10 μm; for printed circuits, they are in general 1 to about 100 μm. If solvents are also used, these are removed after the coating process.

Photocurable compositions such as are used for the various purposes usually contain a number of other additives in addition to the photopolymerizable compounds and the photoinitiators. It is thus often usual to add thermal inhibitors which above all are intended for protection from premature polymerization during preparation of the compositions by mixing of the components. Hydroquinone, hydroquinone derivatives, p-methoxyphenyl, β-naphthols or sterically hindered phenols, such as, for example, 2,6-di(tert-butyl)-p-cresol, for example, are used for this. Small amounts of UV absorbers, for example those of the benztriazole, benzophenone or oxalanilide type, can furthermore be added. Light stabilizers of the sterically hindered amine type (HALS) can likewise be added.

Copper compounds, such as copper naphthenate, stearate or octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine, can be added to increase the stability on storage in the dark.

In order to exclude the inhibiting action of atmospheric oxygen, paraffin or similar waxy substances are frequently added to photocurable mixtures. At the start of the polymerization, these float out because of a lack of solubility in the polymer and form a transparent surface layer which prevents access by air.

Other customary additives are photosensitizers which absorb in certain wavelengths and release the absorbed energy to the initiators or themselves function as an additional initiator. Examples of these are, in particular, thioxanthone, anthracene, anthraquinone and coumarin derivatives.

Other customary additives are accelerators of the amine type, which are of particular importance in pigmented formulations, since they act as chain transfer agents. Examples of these are N-methyldiethanolamine, triethylamine, ethyl p-dimethylaminobenzoate or Michler's ketone. The action of the amines can be intensified by addition of aromatic ketones of the benzophenone type.

Examples of other customary additives are fillers, pigments, dyes, adhesives, wetting agents and flow control agents.

Photocuring is of great importance for printing inks, since the drying time of the binder is a decisive factor for the rate of production of graphics products and should be of the order of fractions of seconds. UV-curable printing inks are of particular importance for screen printing.

The photocurable compositions according to the invention are also suitable for the production of printing plates, in particular flexographic printing plates. Mixtures of soluble linear polyamides or of styrenebutadiene rubber with photopolymerizable monomers, for example acrylamides or acrylates, and a photoinitiator are used, for example, for this. Films and plates of these systems are exposed via the negative (or positive) of the print master and the non-cured portions are then eluted with a solvent.

Another field of use of photocuring is coating of metals, for example in the varnishing of sheet metals for tubes, cans or bottle closures, and photocuring of coatings of plastic, for example of PVC-based floor or wall coverings.

Examples of the photocuring of coatings on paper are colourless varnishing of labels, gramophone record covers or book covers.

The use of the photocurable compositions for imaging processes and for optical production of information carriers is also important. In this instance, the layer applied to the carrier (wet or dry) is irradiated with short-wave light through a photomask and the non-exposed areas of the coating are removed by treatment with a solvent (=developer). The exposed areas are crosslinked polymer and therefore insoluble and remain on the carrier. Visible images are formed after appropriate staining. If the carrier is a metalized layer, after exposure and development the metal can be etched away at the non-exposed areas or reinforced by electroplating. Printed circuits can be produced in this manner. The composition according to the invention can also be used as a photoresist.

Suitable light sources for the exposure to light are those with a high content of short-wave light. Appropriate industrial devices and various types of lamps are available today for this purpose. Examples are carbon arc lamps, xenon arc lamps, mercury vapour lamps, metal-halogen lamps, fluorescent lamps, argon lamps or photographic floodlamps. Laser light sources have also recently been used. These have the advantage that no photomasks are needed; the controlled laser beam writes directly on the photocurable layer.

The invention thus also relates to a) a coated substrate which is coated on at least one surface with a composition according to the invention; b) a process for the photographic production of relief images or coatings, which comprises exposing a coated substrate imagewise or over areas and subsequently removing non-exposed portions with a solvent; c) the use of compounds of the formula Ia as initiators and sensitizers for photopolymerization or photodimerization of non-volatile monomeric, oligomeric or polymeric compounds having at least one photopolymerizable or photodimerizable ethylenically unsaturated double bond; and d) the use of a composition according to the invention for the preparation of varnishes, printing inks, printing plates and resist materials and as an image-recording material and coating agent.

The compounds of the formula I are also useful intermediates for the preparation of substituted tetrathio- and tetraselenotetracenes (cf. U.S. Pat. No. 4,617,151). Electrically conductive charge transfer complexes (CT complexes) can be prepared from such chalcogenated tetracenes with electron acceptors. With the functional substituents thereof, they can be bonded to polymers, for example incorporated into polymers as side groups (cf. U.S. Pat. No. 4,617,151). The CT complexes are also suitable for the production of, for example, antistatic coatings of photographic film elements, magnetic tapes, electrophotographic film elements and electronic components (see U.S. Pat. No. 3,634,336). The chalcogenated tetracenes furthermore have electrochromic properties; they can be used for electrochromic displays. They are also suitable as laser-optical data stores [Nach. Chem. Techn. Lab. 35, page 255 et seq. (1987)] and as the anode material in organic solid state batteries (EP-A-0,090,598). CT complexes of substituted tetrathio- or tetraselenotetracenes can also be incorporated into thermoplastic, thermosetting or elastomeric polymers to achieve antistatic properties. For this, for example, the substituted tetrathio- or tetraselenotetracenes are advantageously dissolved together with a soluble polymer or a precursor thereof, and an electron acceptor, for example a halogen-forming agent (organic halogenated compounds, for example bromoform, trichlorobromomethane, tetrabromomethane, hexachloropropane, perchlorobutadiene, 1,3- or 1,4-dichloro-2- butene, 1,4-bis(trichloromethyl)-benzene, iodoacetonitrile, iodoform, tetrachloroethylene, perchlorocyclobutadiene and N-chloro-, -bromo- or -iodosuccinimide), if appropriate together with another inert solvent, and the excess halogen-forming agent and the solvent are evaporated off at elevated temperature. The composition formed contains a network of needle-shaped crystals of the CT complex in the polymer if the chalcogenated tetracene is unsubstituted or contains small substituents (for example F, CH3 or CF3). Such compositions have a high electrical conductivity. This can be improved further if a substituted tetrathio- or tetraselenotetracene prepared from the compounds of the formula I which forms no such network and is present in the polymer matrix in fine distribution is also used, since such substituted tetrathio- or tetraselenotetracenes have only a low tendency, if any, to crystallize in the polymer. Naphthacene-5,12-diones can furthermore also be used in electrochromic display elements (JP-OS 61-43680).

The compounds of the formula I can also be used for currentless deposition of metals onto the surface of polymers containing hydroxyalkyl groups, for example copolymers of methacrylates with alkyl and hydroxyalkyl ester groups, or epoxy resins which are cured, for example, with amino alcohols. For this, compounds of the formula I are mixed with the polymers, for example in an amount of 0.1 to 10% by weight, based on the polymer, and the mixture is exposed, if appropriate under a negative master, and treated with a metallizing bath which preferably contains a copper salt.

The following examples illustrate the invention in more detail.

A) PREPARATION EXAMPLES

EXAMPLES 1-17

2-n-Octyloxy-naphthacene-5,12-dione 20 g (72.4 mmol) of 2-fluoro-naphthacene-5,12-dione, 94.3 g of 1-octanol, 30.01 g (217.2 mmol) of anhydrous potassium carbonate and 200 ml of dimethyl sulfoxide (DMSO) are stirred at a bath temperature of 100° C. for 20 hours. The reaction mixture is cooled, toluene/dilute hydrochloric acid are added and the organic phase is separated off, washed twice with water, dried with sodium sulfate and evaporated. The residue is washed with pentane and recrystallized from cyclohexane. Yield: 22.9 g (82%), melting point 127°-129° C.

The compounds described in Table 1 are prepared analogously, using the corresponding alcohols.

TABLE 1

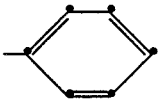

| Example | R | Reaction time (hours) | Bath temp. (°C.) | Yield (%) | melting point (°C.) |
|---|---|---|---|---|---|
| 2 | —CH₂—CH(CH₂—CH₃)—(CH₂)₃—CH₃ | 15 | 130 | 41 | 85–90 |
| 3 | —(CH₂)₂—CH(CH₃)—(CH₂)₃—CH(CH₃)₂ | 16 | 140 | 12 | 102–104 |
| 4 | —CH₂—C≡CH | 23 | 60 | 84 | 160–163 |
| 5 | —H*⁾ | 18 | 130 | 61 | >250 |
| 6 | —CH₃ | 21 | 60 | 94 | 237–239 |
| 7 | —CH₂—CH₃ | 5 | 100 | 95 | 198–200 |
| 8 | —CH(CH₃)₂ | 18 | 127 | 34 | 112–114 |
| 9 | —CH₂—CH(CH₂)(CH₂) (cyclopropyl) | 18 | 110 | 46 | 200–203 |
| 10 | -n-C₁₈H₃₇ | 26 | 120 | 79 | 58–103 |
| 11 |  phenyl | 1 | 100 | 86 | 217–219 |
| 12 | 4-OCH₃-phenyl | ⅓ | 100 | 83 | 222–223 |
| 13 | 4-SCH₃-phenyl | ⅓ | 105 | 84 | 203–205 |

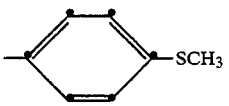

TABLE 1-continued

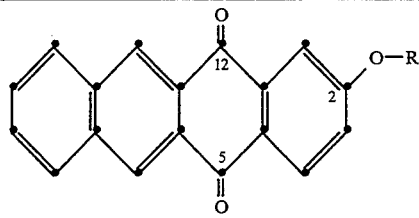

| Example | R | Reaction time (hours) | Bath temp. (°C.) | Yield (%) | melting point (°C.) |
|---|---|---|---|---|---|
| 14 | —(CH₂)₂—O—(CH₂)₂—OH | 3 | 100 | 82 | 130–132 |
| 15 | —CH₂—CH(OH)—CH₂—OH | 3 | 100 | 76 | 187–191 |
| 16 | —(CH₂—CH₂—O)₇CH₃ | 8 | 100 | 72 | 90–93 |
| 17 | —(CH₂—CH₂—O)₁₂—CH₃ | 8 | 100 | 60 | (partly crystalline) |

*)Introduction of H₂S

Examples 18–23

2-(2'-Hydroxyethoxy)-naphthacene-5,12-dione 27.6 g (0.1 mol) of 2-fluoro-5,12-naphthacenequinone, 32.5 g (0.1 mol) of Cs₂CO₃ and 300 ml of ethylene glycol are introduced into a sulfonating flask under nitrogen. After heating to 125° C., the mixture is stirred for 3 h. The reaction mixture is then poured into 3000 ml of water containing hydrochloric acid and the product which has precipitated is filtered off and washed several times with water. After drying in vacuo at 80° C., 30.3 g (97.1%) of pure product are obtained, melting point 208.8° C. The procedure is analogous in Examples 19–23 (see Table 2).

Examples 24–27

2-(3-Butenoxy)-naphthacene-5,12-dione 10 g (0.036 mol) of 2-fluoro-5,12-naphthacenequinone, 26 g (0.028 mol) of Cs₂CO₃ and 10.41 g (0.14 mol) of 3-butanol are introduced into 200 ml of DMF under nitrogen. The reaction mixture is heated to 125° C. and stirred for 4½ h. After precipitation in 4000 ml of water containing hydrochloric acid, the product is filtered off (crude yield 94%). Chromatography on silica gel (CH₂Cl₂) gives 63% pure product; melting point 149° C. The procedure in Examples 25–27 is analogous (see Table 2).

TABLE 2

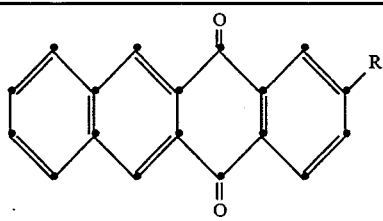

| Example | R | m.p. (°C.) | Reaction time (hours) | Yield (%) | Solvent | Reaction temp. (°C.) |
|---|---|---|---|---|---|---|
| 18 | O—(CH₂)₂—OH | 208 | 3¼ | 97 | i.S. | 125 |
| 19 | O—(CH₂)₄—OH | 190 | 7½ | 70 | i.S. | 120 |
| 20 | O—(CH₂)₆—OH | 153 | 1¼ | 70 | DMSO | 120 |
| 21 | O—(CH₂)₁₀—OH | 113 | ¾ | 73 | i.S. | 125 |
| 22 | O—CH₂—(CF₂)₃—CH₂—OH | 167 | 3¼ | 79 | DMF | 90 |
| 23 | 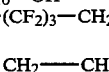 | 144–147 | 19½ | 75 | DMF | 110 |
| 24 | O—CH₂—CH=CH₂ | 164 | 5¼ | 91 | i.S. | 95 |
| 25 | O—(CH₂)₂—CH=CH₂ | 152 | 4½ | 84 | DMF | 130 |
| 26 | O—(CH₂)₄—CH=CH₂ | 125 | 5½ | 78 | DMF | 130 |
| 27 | O—(CH₂)₉—CH=CH₂ | 98 | 5½ | 65 | i.S. | 130 | i.S.: alcohol is identical to the solvent
DMF: dimethylformamide

Examples 28–32

2-(N-Piperidinyl)-naphthacene-5,12-dione 1 g (3.62 mmol) of 2-fluoro-naphthacene-5,12-dione, 0.92 g (10.86 mmol) of piperidine, 1.50 g (10.86 mmol) of potassium carbonate and 10 ml of DMSO are stirred at a bath temperature of 60° C. for 45 minutes. After cooling, the mixture is poured onto water and the orange product is filtered off. The crystals are dissolved in tetrahydrofuran (THF)/toluene and the solution is dried over sodium sulfate and evaporated. The residue is recrystallized from toluene/pentane. Yield: 1.11 g (90%); melting point 230°–233° C.

The procedure in Examples 29–32 is analogous (see Table 3).

TABLE 3

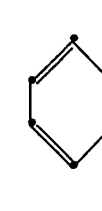

| Example | R | Reaction time (hours) | Bath temp. (°C.) | Yield (%) | m.p. (°C.) |
|---|---|---|---|---|---|
| 29 | —N(Et)₂[1)] | 25 | 50 | 84 | 170–175 |
| 30 | —N(Bu)₂[2)] | 24 | 60 | 69 | 167–170 |
| 31 | 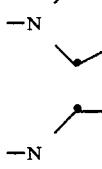 | ½ | 60 | 71 | 245–250 |
| 32 | 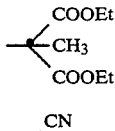 | 7 | 60 | 88 | 230–235 |

[1)]ethyl
[2)]butyl

Example 33

2-(Phenylsulfonyl-)-naphthacene-5,12-dione 1 g (3.62 mmol) of 2-fluoro-naphthacene-5,12-dione, 0.89 g (5.43 mmol) of benzenesulfinic acid sodium salt (sodium benzenesulfinate) and 10 ml of DMSO are stirred at 100° C, for 3 hours. After cooling, the mixture is poured onto water. The crystals are filtered off and dissolved in THF/toluene. The solution is dried over sodium sulfate and evaporated. The residue is recrystallized from THF/toluene/pentane. Yield: 1.35 g (94%), melting point >260° C.

Example 34

2-(Methylsulfonyl-)naphthacene-5,12-dione 2-(Methylsulfonyl-)napthacene-5,12-dione is prepared analogously to Example 33 using sodium methanesulfonate and by stirring at 80° C. for six hours. Yield: 57%.

Example 35

Methyl-(2-naphthacene-5,12-dionyl) sulfoxide a) 2-Methylthio-naphthacene-5,12-dione 3.62 mmol of 2-fluoro-naphthacene-5,12-dione (prepared according to U.S. Pat. No. 4,522,754), 3.98 mmol of NaSCH₃, 10.86 mmol of potassium carbonate and 10 ml of DMSO are stirred at 25° C. for 3 minutes. The mixture is poured onto water. The crystals are filtered off and dissolved in tetrahydrofuran/toluene and the solution is dried over sodium sulfate and evaporated. The residue is recrystallized from THF/toluene/pentane. Yield 1 g (83%); melting point 195°–196° C.

b) Methyl-(2-naphthacene-5,12-dionyl) sulfoxide 10 g (32.86 mmol) of 2-methylthio-naphthacene-5,12-dione, 3.72 g (32.86 mmol) of 30% H₂O₂ and 110 ml of glacial acetic acid are stirred at 80° C. for 4 hours. The mixture is cooled and taken up in methylene chloride/water. The organic phase is separated off, washed three times with water and three times with NaHCO₃ solution, dried over sodium sulfate and concentrated. 7.72 g (73%) of pure sulfoxide are obtained by chromatography (mobile phase: 15% acetone, 85% CH₂Cl₂) over silica gel, melting point 260°–263° C.

Examples 36–40

Dimethyl (2-naphthacene-5,12-dionyl)-malonate 50 g (181 mmol) of 2-fluoro-naphthacene-5,2-dione, 71.74 g (543 mmol) of dimethyl malonate, 75.04 g (543 mmol) of potassium carbonate and 500 ml of DMSO are stirred at a bath temperature of 100° C. for 2 hours. After cooling, the mixture is poured onto dilute hydrochloric acid. The precipitate is filtered off, washed with water and methanol and then recrystallized from toluene. Yield 63.97 g (91%); melting point 211°–215° C.

The procedure in Examples 37 to 40 is analogous (see Table 4):

TABLE 4

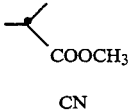

| Example | R | Reaction time (hours) | Bath temp. (°C.) | Yield (%) | m.p. (°C.) |
|---|---|---|---|---|---|
| 37 | COOEt, CH₃, COOEt | 2 | 100 | 79 | 134–140 |
| 38 | CN, COOCH₃ | 24 | 60 | 75 | 210–215 |
| 39 | CN, COOEt | 3 | 60 | 73 | 212–217 |
| 40 | 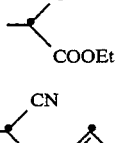 | 42 | 60 | 44 | 220–223 |

Example 41

(2-Naphthacene-5,12-dionyl)-acetic acid 8 g (20.6 mmol) of dimethyl (2-naphthacene-5,12-dionyl)-malonate (Example 36), 60 ml of glacial acetic acid and 60 ml of concentrated HCl solution are stirred under reflux for 4.5 hours. The mixture is poured onto ice/water. The crystals are filtered off, washed with diethyl ether and recrystallized from THF/pentane. Yield 4.88 g (75%); melting point >220° C.

Example 42

1-Nitro-naphthacene-5,12-dione 30 g (147.7 mmol) of 5-nitronaphtho-1,4-quinone, 58.02 g (about 220 mmol) of 1,2-dibromobenzocyclobutene (contaminated with a little 1-iodo-2-bromobenzocyclobutene) and 300 ml of toluene are stirred under reflux for 2 days, the hydrobromic acid formed being distilled off together with a little toluene and the toluene lost in this way being replaced by fresh toluene. The mixture is cooled to 25° C. and the precipitate is filtered off, washed with toluene and dried in vacuo at 140° C. Yield: 43.46 g (97%); melting point >250° C. The product can be recrystallized from -butyrolactone; yield; 77%.

Examples 43–51

1-Phenoxy-naphthacene-5,12-dione 3 g (9.9 mmol) of 1-nitronaphthacene-5,12-dione (Example 42), 2.73 g (19.8 mmol) of potassium carbonate, 1.39 g (14.8 mmol) of phenol and 30 ml of DMSO are stirred at a bath temperature of 100° C. for 6 hours. After cooling, the mixture is partitioned between methylene chloride/dilute hydrochloric acid. The organic phase is separated off, washed with water, dried over sodium sulfate and evaporated. The product is obtained in a pure form by chromatography on silica gel (mobile phase: methylene chloride); yield 2.52 g (73%); melting point 195°–200° C.

The procedure in Examples 44–51 is analogous (see Table 5):

The mixture is cooled and dilute hydrochloric acid is added. The product is filtered off, washed with water, dried and chromatographed with methylene chloride on silica gel. Sublimation under $1.3 \times 10^{-1}$ bar/18-0°–310° C. gives 0.26 g (25%) of pure product, melting point >250° C.

Example 53

2,3-Dimethoxy-naphthacene-5,12-dione 1 g (3.4 mmol) of 2,3-difluoro-naphthacene-5,12-dione, 0.94 g (6.8 mmol) of $K_2CO_3$, 2.18 g of methanol and 20 ml of DMSO are stirred at 110° C. for 22 hours. The mixture is poured onto dilute hydrochloric acid. The product is filtered off, washed four times with water, dried and recrystallized from $CH_2Cl_2$/pentane; yield 0.72 g (67%); melting point >250° C.

Example 54

2-Fluoro-3-(N-morpholino-)-naphthacene-5,12-dione 1 g (3.4 mmol) of 2,3-difluoro-naphthacene-5,12-dione, 0.94 g (6.8 mmol) of potassium carbonate, 1.48 g (17 mmol) of morpholine and 20 ml of THF are stirred under reflux for 23 hours. The mixture is poured onto

TABLE 5

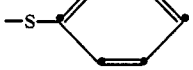

| Example | R | Reaction time (hours) | Bath temp. (°C.) | Yield (%) | m.p. (°C.) |
|---|---|---|---|---|---|
| 44 | —OCH$_3$ | 23 | 100 | 68 | 260–262 |
| 45 | —SCH$_3$*) | ½ | 25 | 56 | 260–265 |
| 46 | —S—CH$_2$CH$_3$ | 1 | 25 | 48 | 200–205 |
| 47 | —S—CH$_2$—CH$_2$—OH | 1,5 | 25 | 30 | 250–255 |
| 48 |  | 1,5 | 25 | 54 | 255–258 |
| 49 |  | 24 | 80 | 39 | 210–215 |
| 50 | | 20 | 80 | 65 | 205–206 |
| 51 | 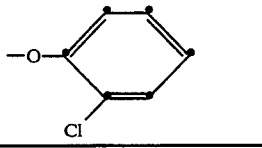 | 20 | 80 | 28 | 205–206 |

*)NaSCH$_3$ is used here instead of the mercaptan.

Example 52

2-Fluoro-3-methoxy-naphthacene-5,12-dione 1 g (3.4 mmol) of 2,3-difluoronaphthacene-5,12-dione, 0.94 g (6.8 mmol) of potassium carbonate, 3.24 g of methanol and 20 ml of tetrahydrofuran (THF) are stirred at 25° C. for 18 hours and under reflux for 3 days.

water. The product is filtered off, washed with water, dried and recrystallized from dioxane; yield 0.78 g (64%); melting point >240° C.

Example 55

Dimethyl 2-(3-fluoro-naphthacene-5,12-dionyl)-malonate 1 g (3.4 mmol) of 2,3-difluoro-naphthacene-5,12-dione, 0.94 g (6.8 mmol) of potassium carbonate, 0.89 g (6.8 mmol) of dimethyl malonate and 20 ml of DMSO are stirred at 50° C. for 22 hours. The mixture is poured onto dilute hydrochloric acid and extracted with THF/toluene. The organic phase is washed with water, dried over sodium sulfate and evaporated. The product is purified by chromatography over silica gel (mobile phase: 1% acetone/99% $CH_2Cl_2$); yield 1.25 g (91%); melting point 225°–230° C.

Example 56

2-Cyano-naphthacene-5,12-dione 10 g (33.2 mmol) of naphthacene-5,12-dione-2-carboxamide, 10.18 g (66.4 mmol) of $POCl_3$ and 200 ml of DMF are stirred at 10° C. and then at 25° C. for 2 hours. The mixture is poured onto ice-water. The precipitate is filtered off, washed three times with water and dried. When recrystallized from o-dichlorobenzene, 7.35 g (78%) of crude product are obtained.

IR spectrum (KBr): 1678 $cm^{-1}$: Quinone; 2240 $cm^{-1}$: CN Mass spectrum: M/e=283 ($M^+$) (base peak); 255; 227; 226; 100.

Example 57

2-(Trifluoromethyl-)-naphthacene-5,12-dione 5.65 g (25 mmol) of 6-(trifluoromethyl)-1,4-naphthoquinone, 9.82 g (about 37 mmol) of 1,2-dibromobenzocyclobutene (contaminated with a little 2-bromo-1-iodobenocyclobutene) and 100 ml of xylene are kept under reflux for 16 hours, using a water separator. The mixture is cooled and the precipitate is filtered off and washed with xylene. Yield 5.82 g (71%); melting point 253°–254° C. The procedure in Examples 58 to 61 is analogous.

Example 58

2,3-bis-(Trifluoromethyl)-naphthacene-5,12-dione; yield 59%; melting point >280° C.

Example 59

Methyl 1-(trifluoromethyl)-naphthacene-5,12-dione-3-carboxylate; yield 60%. melting point 234°–235° C.

Example 60

Methyl 2-ethoxy-naphthacene-5,12-dione-3-carboxylate; yield 30%; melting point 192°–194° C.

Example 61

Diethyl 2-ethoxy-naphthacene-5,12-dione-3-dicarboxylate; yield 41%; melting point 163°–164° C.

Starting substances:

The substituted naphthoquinones of Examples 57 to 60 are obtained by a Diels-Alder reaction of corresponding α-pyrones with p-benzoquinone, the trifluoromethyl derivatives being prepared by fluorination of the carboxylic acid ethyl ester with $HF/SF_4$. The naphthoquinone of Example 60 is obtained by a Diels-Alder reaction of 1-ethoxy-2,4-dicarbethoxy-1,4-butadiene with p-benzoquinone.

Examples 62–64

A mixture of 1 mol of the appropriately substituted dibromo- or bromoiodo-benzocyclobutene[1], 1.5 mol of naphthoquinone and 7 liters of solvent is heated under reflux for 4–16 hours. After cooling, the naphthacenequinone which has precipitated is filtered off and purified by crystallization or sublimation under a high vacuum (see Table 6)

TABLE 6

| Example No. | R | Solvent | Reaction time (hours) | Yield (%) | m.p. (°C.) | Mass spectrum ($M^+$/%) |
|---|---|---|---|---|---|---|
| 62[1] | —Br | Xylene | 16 | 50 | >270 | 336/90 |
| 63[1] | —COOCH₃ | Dichlorobenzene | 16 | 10 | 268 | 316/100 |
| 64[2] | —NO₂ | Dichlorobenzene | 4 | 22 | >270 | 303/100 |

[1] recrystallized from toluene
[2] sublimed at 200° C.
[1] prepared by reaction of appropriately substituted o-dihalogeno-methyl-benzenes with NaI in acetonitrile at 80° C.

Examples 65–95

A mixture of 0.1 mol of appropriately substituted bis-dibromomethylbenzene, 0.12–0.2 mol of unsubstituted or substituted naphthoquinone, 0.6 mol of sodium iodide and 1000 ml of acetone or acetonitrile is boiled under reflux for 2–6 hours, while stirring and under an $N_2$ atmosphere. After cooling, the precipitate which has separated out is filtered off and digested with water. The substituted naphthacenedione obtained in this manner is either recrystallized or sublimed under a high vacuum for further purification (cf. Tables 7, 8 and 9).

TABLE 7

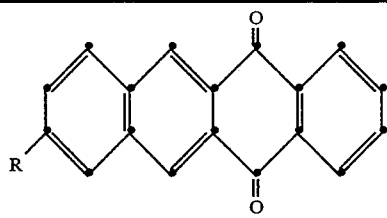

| Example No. | R | Solvent | Reaction time (hours) | Recrystallization/sublimation | Yield (%) | m.p. (°C.) | Mass spectrum ($M^+$/%) |
|---|---|---|---|---|---|---|---|
| 65[a] | Me₃Si | Acetonitrile | 5 | Sublim. 150° C. | 79 | 168–170 | |
| 66 | F | Acetonitrile | 2 | Sublim. 200° C. | 68 | >270 | 276/100 |

[a] The filtrate is evaporated to dryness, the residue is dissolved in $CH_2Cl_2$ and the solution is washed with $NAHSO_3$ and dried. The residue is then subjected to steam distillation and the non-volatile portions are extracted with ether, dried and then sublimed.

TABLE 8

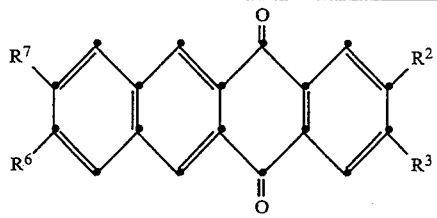

| Example No. | $R^6$ | $R^7$ | $R^2$ | $R^3$ | Solvent | Reaction time (hours) | Recrystallization/ sublimation | Yield (%) | m.p. (°C.) | Mass spectrum ($M^+/\%$) |
|---|---|---|---|---|---|---|---|---|---|---|
| 67 | OCH₃ | H | CF₃ | CF₃ | Acetonitrile | 5 | Sublim. 200° C. | 33 | >280 | 424/100 |
| 68 | OCH₃ | H | COOEt | COOEt | Acetonitrile | 5 | Sublim. 180° C. | 40 | 214–216 | 432/90 |
| 69 | OCH₃ | H | CH₃ | CH₃ | Acetone | 5 | Sublim. 180° C. | 13 | 268–270 | 316/100 |
| 70 | Me₃Si | Me₃Si | H | H | Acetonitrile | 3 | Sublim. 180° C. | 70 | 196–197 | 405/55 |
| 71[b] | Me₃Si | Me₃Si | COOEt | COOEt | Acetonitrile | 3 | Isopropyl ether | 64 | 138–139 | 546/80 |
| 72 | CN | CN | COOEt | COOEt | CH₃CN | 5 | Sublim. | 44 | >270 | 452/10 |
| 73 | CN | CN | H | H | CH₃CN | 5 | Sublim. | 71 | >270 | 308/100 |
| 74 | Br | Br | H | H | CH₃CN | 4 | Sublim. | 60 | >250 | 416/100 |
| 75 | Br | Br | COOEt | COOEt | CH₃CN | 4 | Sublim. | 53 | >250 | 560/64 |
| 76 | Br | Br | CF₃ | CF₃ | CH₃CN | 4 | Sublim. | 58 | >250 | 552/100 |
| 77 | CF₃ | CF₃ | Cl | COOEt | CH₃CN | 6 | Sublim. | 68 | >270 | 500/60 |
| 78 | CF₃ | CF₃ | CF₃ | CF₃ | CH₃CN | 8 | Sublim. | 70 | >280 | 530/100 |
| 79 | CF₃ | H | COOEt | COOEt | Acetone | 5 | Sublim. | 60 | 216–217 | 470/40 |
| 80 | CF₃ | H | CF₃ | CF₃ | Acetone | 5 | Sublim. | 55 | 261–262 | 462/100 |
| 81 | Cl | Cl | H | H | CH₃CN | 5 | Sublim. | 54 | >250 | 326/100 |
| 82 | Cl | Cl | CF₃ | CF₃ | CH₃CN | 5 | Sublim. | 41 | >250 | 462/100 |
| 83 | Cl | Cl | COOEt | COOEt | CH₃CN | 5 | Sublim. | 68 | >250 | 470/48 |
| 84 | COOMe | COOMe | H | H | CH₃CN | 4 | Sublim. | 67 | >250 | 374/48 |
| 85 | COOMe | COOMe | COOEt | COOEt | CH₃CN | 4 | Sublim. | 70 | 238–239 | 518/88 |
| 86 | COOMe | COOMe | CF₃ | CF₃ | CH₃CN | 5 | Sublim. | 72 | >250 | 510/40 |
| 87 | Me₃Si | Me₃Si | CF₃ | CF₃ | CH₃CN | 5 | Isopropyl ether | 30 | 143–145 | 538/60 |

[b]The filtrate is evaporated to dryness, the residue is dissolved in ether and the solution is washed with NaHSO₃ and dried. The ether residue is filtered over a silica gel column with CH₂Cl₂.

TABLE 9

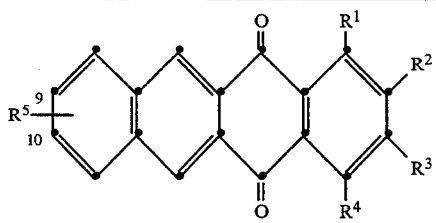

| Example No. | $R^1$ | $R^2$ | $R^3$ | $R^4$ | $R^5$ | Solvent | Reaction time (hours) | sublimation (°C.) | Yield (%) | m.p. (°C.) | Mass spectrum ($M^+/\%$) |
|---|---|---|---|---|---|---|---|---|---|---|---|
| 88 | H | COOCH₃ | H | H | OCH₃ | Acetone | 5 | 180 | 50 | 246–248 | 346/95 |
| 89 | NO₂ | H | H | H | OCH₃ | Acetone | 5 | 180 | 28 | >280 | 333/95 |
| 90 | CF₃ | H | COOCH₃ | H | OCH₃ | Acetone | 5 | 200 | 80 | 235–240 | 414/100 |
| 91 | COOEt | OEt | COOEt | H | OCH₃ | Acetone | 5 | 220 | 16 | 230–232 | 476/60 |
| 92 | H | COOCH₃ | H | CF₃ | CF₃ | CH₃CN | 6 | 240 | 50 | >280 | 452/100 |
| 93 | H | Cl | COOEt | H | CF₃ | CH₃CN | 6 | 230 | 60 | >280 | 432/70 |
| 94[1] | H | F | H | H | F | Fluorobenzene | 4 | 225 | 47 | 278–280 | 294/100 |
| 95 | H | Cl | H | H | F | CH₃CN | 6 | 270 | 26 | >280 | 310/100 |

These antracenediones are in the form of an approx. 1:1 mixture of the two possible isomers (—OCH₃ bonded in the 8- or 9-position).
[1]Catalyst: AlCl₃.

B) USE EXAMPLES

Example 96

Photocuring of an acrylate mixture for the preparation of a relief image.

A photocurable composition is prepared by mixing the following components:

| | | Solids content |
|---|---|---|
| 150.30 g | of Scripset 540[1] (30% solution in acetone) | 45.1 g |
| 48.30 g | of trimethylolpropane triacrylate | 48.3 g |
| 6.60 g | of polyethylene glycol diacrylate | 6.6 g |
| 0.08 g | of crystal violet | |
| 205.28 g | | 100.0 g |

[1]Polystyrene/maleic acid half-ester copolymer (Monsanto)

Portions of this composition are mixed with 0.2% (based on the composition) of the photoinitiators listed in the following table. All the operations are performed under red light or yellow light.

The samples to which initiator has been added are applied with a spiral doctor of 150 μm to 200 μm aluminium foil (10×15 cm). The solvent is removed by heating at 60° C. in a circulating air oven for 15 minutes. A dry layer thickness of about 35 μm results. A 76 μm thick polyester film is placed on the layer, and a standardized test negative with 21 steps of different optical density (Stouffer wedge) is placed on this. A second polyester film is placed on top and the laminate thus obtained is fixed onto a metal plate by means of vacuum. The sample is then exposed to a 5 KW metal halide lamp (type MO 23) at a distance of 30 cm, and in particular for 20 seconds in a first test series and for 40 seconds in a second test series. After the exposure, the films and mask are removed and the exposed layer is developed in a ultrasonic bath with developer A for 2 minutes and then dried at 60° C. in a circulating air oven for 15 minutes. The sensitivity of the initiator system used is characterized by stating the last wedge step imaged without tackiness. The higher the number of steps, the more sensitive the system. An increase by two steps here means approximately a doubling of the rate of curing. The results are shown in Table 10. Developer A contains 15 g of sodium metasilicate.9 H$_2$O; 0.16 g of KOH; 3 g of polyethylene glycol 6000; 0.5 g of levulinic acid and 1000 g of deionized water.

TABLE 10

| Photoinitiator Naphthacenedione of example | No. of steps imaged | |
|---|---|---|
| | after 20 sec. | after 40 sec. exposure |
| 2 | 3 | 5 |
| 7 | 2 | 4 |
| 35 | 3 | 5 |
| 37 | 2 | 4 |
| 44 | 5 | 7 |
| 88 | 1 | 2 |
| A[1] | 3 | 5 |
| B[2] | 2 | 4 |

[1] Methyl 2-anthracene-5,12-dionecarboxylate
[2] 6-Methoxyanthracene-5,12-dione Example 97

A solution having the composition:

| Ethylcellosolve | 71.00 g |
|---|---|
| Scripset 550*[) | 14.00 g |
| Trimethylolpropane triacrylate | 15.00 g |
| Polyethylene glycol 200 diacrylate | 2.00 g |

*[) Styrene/maleic acid monoester copolymer (M$_w$ = 10000, acid no. 190), manufacturer Monsanto is divided into equal portions of 10 grams each. In each case 0.05 g of naphthacenedione and 0.5 g of glycerol are dissolved in this solution under red light.

Coatings are applied with a wire doctor in a wet film thickness of 12 micrometers onto transparent polyester film. The wet films are dried at 80° C. in a circulating air oven for 30 minutes.

An oxygen barrier layer 0.5 micrometers thick is applied by dipping into a solution of

| Mowiol 4-88 (polyvinyl alcohol) | 30.00 g |
|---|---|
| Brij 35 (10% in water)**[) | 15.00 g |
| Deionized water | 250.00 g |

**[) Polyoxyethylene lauryl ether (wetting agent, manufacturer Atlas Powder)

and subsequent drying at 80° C. in a circulating air oven.

The dry film is exposed with a 5000 W mercury lamp (MO 33, Staub, Neu Isenburg) through a step wedge with increments of 0.15 (log O.D.) and then developed in a solution having the composition

| Sodium metasilicate nonahydrate | 15.00 g |
|---|---|
| Strontium hydroxide octahydrate | 0.30 g |
| Polyglycol 6000 | 3.00 g |
| Levulinic acid | 0.50 g |
| Deionized water | 1000.00 g | to give a relief image. The light intensity is measured with a Powermeter from Oriel with a 365 nm sensor. Table 11 shows the exposure energy required to achieve step 7 of the step wedge.

TABLE 11

| Naphthacenedione of Example | UV spectrum (extinction at $\lambda_{max}$) | WP$_7$ mJ/cm$^{-2}$) |
|---|---|---|
| 37 | $\epsilon = 6100$, $\lambda_{max}$: 398 nm shoulder at 414 nm | 660 |

Example 98

Photometallization

A copolymer of 65 mol % of hydroxypropyl methacrylate and 35 mol % of methyl methacrylate having a molecular weight of 120000 Daltons (measured by light scattering in dioxane at 25° C.) is dissolved in DMF, and 5 mol % of anthracenedione according to Example 37 (based on the polymer hydroxyl groups) is added. Films are produced by doctor-coating the solution onto a polyester carrier and subsequent drying at 80° C. in a circulating air oven for 2 hours. The films are exposed on a thermostatically controllable vacuum heating bench at 50° C. under a negative using a Hg high pressure lamp of 40 mW/cm$^{-2}$ intensity. A dark negative image of the master is obtained and is reinforced in a deposition bath having the composition

| CuSO$_4$ × 5H$_2$O | 0.0665 mol/l |
|---|---|
| HCOH | 0.0467 mol/l |
| Quadrol | 0.0599 mol/l |
| NaOH | pH 12.6 |
| NaCN | 25 mg/l |
| 2-Mercaptobenzothiazole | 10 mg/l | at 45° C. to give a copper image.

Example 99

Sensitization of 2+2 cycloaddition 5% (w/w) of 2-methoxy-anthracene-5,12-dione is dissolved in a 20% (w/w) solution of a copolymer having a molecular weight of 140000 Daltons (measured by light scattering in dioxane at 25° C.) and consisting of 20 mol % of ethyl acrylate and 80 mol % of N-(5-methyl-3-oxa-4-oxohexen-5-yl)-dimethylmaleimide (prepared by the process in Angew. Makromol, Chem. 115 (1983) 163 et seq.). The solution is doctor-coated with a wire doctor as a film in a wet film thickness of 24 μm onto a copper-coated glass fibre-epoxide laminate and dried at 80° C. for 1 hour. The dry film is exposed with a 5000 W mercury lamp (MO 33, Staub) through a step wedge with increments of 0.15 (log O.D.) and then developed in 1,1,1-trichloroethane to give a relief image. The exposure energy required to achieve step 7 of the step wedge is 231 mJ×cm$^{-2}$.

What is claimed is:

1. A compound of the formula

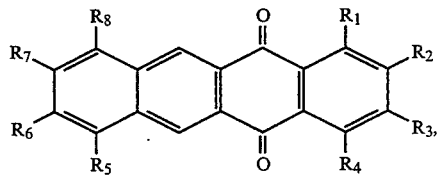

wherein (a) $R_5$, $R_6$, $R_7$ and $R_8$ are H, and (a1) $R_1$ and $R_4$ are independently of each other selected from the group consisting of H, $-NO_2$, $-CF_3$, $-CN$, $COOR_9$, $-CONR_9R_{10}$, $-COCl$, $-Si(C_1-C_4alkyl)_3$, $-S(C_mH_{2m}-O-)_nR_{11}$, $-O(C_mH_{2m}-O-)_nR_{11}$, substituted or unsubstituted $C_1-C_{20}alkyl-(X_1-)_p$, $C_2-C_{18}alkenyl-(X_1-)_p$, $C_2-C_{18}alkynyl-(X_1-)_p$, $C_3-C_8cycloalkyl-(X_1-)_p$, $(C_1-C_{12}alkyl)C_3-C_8cycloalkyl-(X_1-)_p$, $C_3-C_8cycloalkylC_rH_{2r}-(X_1-)_p$, $(C_1-C_{12}alkyl)C_3-C_8cycloalkyl\ C_rH_{2r}-(X_1-)_p$, phenyl-$(X_1-)_p$, $(C_1-C_{12}alkyl)phenyl-(X_1-)_p$, phenylC$_rH_{2r}-(X-)_p$, $(C_1-C_{12}alkyl)phenylC_rH_{2r}-(X-)_p$, substituted $C_1-C_{20}alkylthio$ and phenyloxy, $(C_1-C_{12}alkyl)$phenyloxy or $C_1-C_{20}alkoxy$ which is substituted by halogen, $-CN$, $-NR_9R_{10}$, $-SR_9$, $-OR_9$ or $-COOR_9$, wherein $R_1$ is additionally selected from the group consisting of unsubstituted $C_1-C_{20}alkylthio$, phenyloxy, phenylthio, $C_1-C_{12}alkylphenyloxy$ and substituted $C_1-C_{12}alkylphenylthio$; and (a2) $R_2$ and $R_3$ each are independently selected from the group consisting of H, substituted $C_5-C_{20}alkyl$, unsubstituted $C_8-C_{18}alkoxy$, substituted $C_3-C_{20}alkoxy$, unsubstituted or substituted $C_1-C_{20}alkyl-(X_1-)_p-$, phenyl-$(X)_p-$, $(C_1-C_{12}alkyl)$-phenyl-$(X-)_p$, phenylC$_rH_{2r}-(X-)_p$, $(C_1-C_{12}alkyl)phenylC_rH_{2r}-(X-)_p$, $C_2-C_{18}alkenyl-(X-)_p$, $C_2-C_{18}alkynyl-(X-)_p$, $C_3-C_8cycloalkyl-(X-)_p$, $(C_1-C_{12}alkyl)C_3-C_8cycloalkyl-(X-)_p$, $C_3-C_8cycloalkylC_rH_{2r}-(X-)_p-$, and $(C_1-C_{12}alkyl)$-$C_3-C_8cycloalkylC_rH_{2r}-(X-)_p$, or (a3) one of $R_2$ and $R_3$ or both of $R_2$ and $R_3$ are selected from the group consisting of $C_1-C_4alkyl$ which is substituted by halogen, $-CN$, $-NR_9R_{10}$, $-SR_9$, $-OR_9$ or $-COOR_9$ and $C_1-C_2-alkoxy$ which is substituted by halogen, $-CN$, $-NR_9R_{10}$, $-SR_9$, $-OR_9$ $-COOR_9$, or (a4) one of $R_2$ and $R_3$ or both of $R_2$ and $R_3$ are selected from the group consisting of $-SH$, $-NO_2$, $-CF_3$, $-NR_9R_{10}$, $-O(C_mH_{2m}-O-)_nR_{11}$, and $-Si(C_1-C_4alkyl)_3$, or (a5) one of $R_2$ and $R_3$ is halogen, $-COOR_9-NR_9R_{10}$ or COCl and the other of $R_2$ and $R_3$ is selected from the group consisting of $-NO_2$, $-CF_3$, $-CN$, $-NR_9R_{10}$, $-SH$, $-O(C_mH_{2m}-O-)_nR_{11}$, $-Si(C_1-C_4alkyl)_3$, $C_1-C_{20}alkyl-(X-)_p$, $C_2-C_{18}alkenyl-(X-)_p$, $C_2-C_{18}alkynyl-(X-)_p$, $C_3-C_8-cycloalkyl-(X-)_p$, $(C_1-C_{12}alkyl)-C_3-C_8cycloalkyl-(X-)_p$, $C_3-C_8cycloalkylC_rH_{2r}-(X-)_p$, $(C_1-C_{12}alkyl)C_3-C_8cycloalkylC_rH_{2r}-(X-)_p$, phenyl-$(X-)_p$, $(C_1-C_{12}alkyl)phenyl-(X-)_p$, phenylC$_rH_{2r}-(X-)_p$, and $(C_1-C_{12}alkyl)phenylC_rH_{2r}-(X-)_p$, which are unsubstituted or substituted, or the other of $R_2$ and $R_3$ is H, if at least one or $R_1$ and $R_4$ is not hydrogen, or (a6) $R_2$ and $R_3$ together are $-CO-O-CO-$ or $-CO-NR_9-CO-$ and at least one of $R_1$ and $R_4$ is not hydrogen; and wherein $X_1$ is $-SO-$ or $-SO_2-$ and X is $-O-$, $-SO-$ or $-SO_2-$;

$R_9$ and $R_{10}$ independently of one another are $C_1-C_{12}alkyl$, phenyl or $(-C_mH_{2m}-O-)_qR_{11}$, or $R_9$ and $R_{10}$ together are tetramethylene, pentamethylene, 3-oxapentylene or $-CH_2CH_2NR_9CH_2CH_2-$, $R_{11}$ is H or $C_1-C_{12}alkyl$, m is a number from 2 to 4, n is a number from 2 to 20, p is 1, q is a number from 1 to 20 and r is 1 or 2; and wherein substituted $R_1$, $R_2$, $R_3$ and $R_4$ groups are substituted by halogen, $-CN$, furfuryl, $-NR_9R_{10}$, $-OR_9$, $-SR_9$ or $COOR_9$ unless otherwise specified;

with the provisos that at least one of $R_1$, $R_2$, $R_3$ or $R_4$ is other than hydrogen.

2. A compound of claim 1 wherein $R_1$ is $-NO_2$, $-CF_3$ or $-COO(C_1-C_4alkyl)$;

$R_4$ is H; and $R_2$ and $R_3$ are independently of one another $C_3$ to $C_{18}alkoxy$, $C_3-C_{12}hydroxyalkyl$ or $C_3-C_6dihydroxyalkyl$; $C_3-C_{12}alkenoxy$ or $C_3-C_6alkynoxy$, in which the $-O-$ atom is not bonded to the alkene or alkyne group, or $-O-(CH_2CH_2-O-)_nR^{11}$ where n is 2 to 12 and $R^{11}$ is H or $C_1-C_6alkyl$; phenyloxy which is unsubstituted or substituted by $-F$, $-Cl$, $C_1-C_4alkyl$, $C_1-C_4alkoxy$ or $C_1-C_4alkylthio$; $-NR^9R^{10}$, where $R^9$ and $R^{10}$ are $C_1-C_6alkyl$, or together are pentamethylene or 3-oxapentylene; $C_1-C_6-alkyl-SO-$, $C_1-C_6alkyl-SO_2-$, phenyl-SO$-$ or phenyl-SO$_2-$; $C_1-C_4alkyl$ or benzyl which are substituted by $-CN$ or $COO(C_1-C_6alkyl)$; or CN, $-CF_3$, $-F$, $-Cl$ or $-Br$.

3. A compound of claim 1 wherein (b1) $R_1$ and $R_4$ are independently of each other selected from the group consisting of H, $-NO_2$, $-CF_3$, $-CN$, $COOR_9$, $-CONR_9R_{10}$, $-COCl$, $-Si(C_1-C_4alkyl)_3$, $-S(C_mH_{2m}-O-)_nR_{11}$, $-O(C_mH_{2m}-O-)_nR_{11}$, substituted or unsubstituted $C_1-C_{20}alkyl-(X_1-)_p$, $C_2-C_{18}alkenyl-(X_1-)_p$, $C_2-C_{18}alkynyl-(X_1-)_p$, $C_3-C_8cycloalkyl-(X_1-)_p$, $(C_1-C_{12}alkyl)C_3-C_8cycloalkyl-(X_1-)_p$, $C_3-C_8cycloalkylC_rH_{2r}-(X_1-)_p$, $(C_1-C_{12}alkyl)C_3-C_8cycloalkyl\ C_rH_{2r}-(X_1-)_p$, phenyl-$(X_1-)_p$, $(C_1-C_{12}alkyl)phenyl-(X_1-)_p$, phenylC$_rH_{2r}-(X-)_p$, $(C_1-C_{12}alkyl)phenylC_rH_{2r}-(X-)_p$, substituted $C_1-C_{20}alkylthio$ and phenyloxy or $(C_1-C_{12}alkyl)$phenyloxy which is substituted by halogen, $-CN$, $-NR_9R_{10}$, $-SR_9$, $-OR_9$ or $-COOR_9$, wherein $R_1$ is not $-COOH$ if $R_2$, $R_3$ and $R_4$ are H; and wherein $R_1$ is additionally selected from the group consisting of unsubstituted $C_1-C_{20}alkylthio$, phenyloxy, phenylthio, $C_1-C_{12}alkylphenyloxy$ and substituted $C_1-C_{12}alkylphenylthio$; and (b2) $R_2$ and $R_3$ each are independently selected from the group consisting of H, $-SH$, $-NO_2$, $-CF_3$, $-NR_9R_{10}$, $-O(C_mH_{2m}-O-)_nR_{11}$, $-Si(C_1-C_4alkyl)_3$, unsubstituted or substituted $C_1-C_{20}alkyl-(X_1-)_p-$, phenyl-$(X)_p-$, $(C_1-C_{12}alkyl)phenyl-(X-)_p$, phenylC$_rH_{2r}-(X-)_p$, $(C_1-C_{12}alkyl)$-phenylC$_rH_{2r}-(X-)_p$, $C_2-C_{18}alkenyl-(X-)_p$, $C_2-C_{18}alkynyl-(X-)_p$, $C_3-C_8cycloalkyl-(X-)_p$, $(C_1-C_{12}alkyl)C_3-C_8cycloalkyl-(X-)_p$, $C_3-C_8cycloalkylC_rH_{2r}-(X-)_p-$, $(C_1-C_{12}alkyl)C_3-C_8cycloalkylC_rH_{2r}-(X-)_p$.

4. A compound of claim 1 wherein (c1) $R_1$ and $R_4$ are independently of each other selected from the group consisting of H, —$NO_2$, —$CF_3$, —CN, $COOR_9$, —$CONR_9R_{10}$, —COCl, —Si($C_1$-$C_4$alkyl)$_3$, —S($C_mH_{2m}$—O—)$_nR_{11}$, —O($C_mH_{2m}$—O—)$_nR_{11}$, substituted or unsubstituted $C_1$-$C_{20}$alkyl-($X_1$—)$_p$, $C_2$-$C_{18}$alkenyl-($X_1$—)$_p$, $C_2$-$C_{18}$alkynyl-($X_1$—)$_p$, $C_3$-$C_8$cycloalkyl-($X_1$—)$_p$, ($C_1$-$C_{12}$alkyl)$C_3$-$C_8$cycloalkyl-($X_1$—)$_p$, $C_3$-$C_8$cycloalkyl$C_rH_{2r}$—($X_1$—)$_p$, ($C_1$-$C_{12}$alkyl)$C_3$-$C_8$cycloalkyl$C_rH_{2r}$—($X_1$—)$_p$, phenyl-($X_1$—)$_p$, ($C_1$-$C_{12}$alkyl)phenyl-($X_1$—)$_p$, phenyl$C_rH_{2r}$—($X_1$—)$_p$, ($C_1$-$C_{12}$alkyl)phenyl$C_rH_{2r}$—($X_1$—)$_p$, substituted $C_1$-$C_{20}$alkylthio and phenyloxy or ($C_1$-$C_{12}$alkyl)phenyloxy which is substituted by halogen, —CN, —$NR_9R_{10}$, —$SR_9$, —$OR_9$ or —$COOR_9$, wherein $R_1$ is not —COOH if $R_2$, $R_3$ and $R_4$ are H; and wherein $R_1$ is additionally selected from the group consisting of unsubstituted $C_1$-$C_{20}$alkylthio, phenyloxy, phenylthio, $C_1$-$C_{12}$alkylphenyloxy and substituted $C_1$-$C_{12}$alkylphenylthio; and (c5) one of $R_2$ and $R_3$ is halogen, —$COOR_9$ —$NR_9R_{10}$ or COCl and the other of $R_2$ and $R_3$ is selected from the group consisting of —$NO_2$, —$CF_3$, —CN, —$NR_9R_{10}$, —SH, —O($C_mH_{2m}$—O—)$_nR_{11}$, —Si($C_1$-$C_4$alkyl)$_3$, $C_1$-$C_{20}$alkyl-(X—)$_p$, $C_2$-$C_{18}$alkenyl-(X—)$_p$, $C_2$-$C_{18}$alkynyl-(X—)$_p$, $C_3$-$C_8$cycloalkyl-(X—)$_p$, ($C_1$-$C_{12}$alkyl)$C_3$-$C_8$cycloalkyl-(X—)$_p$, $C_3$-$C_8$cycloalkyl$C_rH_{2r}$—(X—)$_p$, ($C_1$-$C_{12}$alkyl)$C_3$-$C_8$cycloalkyl$C_rH_{2r}$—(X—)$_p$, phenyl-(X—)$_p$, ($C_1$-$C_{12}$alkyl)phenyl-(X—)$_p$, phenyl$C_rH_{2r}$—(X—)$_p$, and ($C_1$-$C_{12}$alkyl)phenyl$C_rH_{2r}$—(X—)$_p$, which are unsubstituted or substituted, or the other of $R_2$ and $R_3$ is H, if at least one or $R_1$ and $R_4$ is not hydrogen.

5. A compound of claim 1 wherein $R_2$ and $R_3$ together are —CO—O—CO— or —CO—$NR_9$—CO— and at least one of $R_1$ and $R_4$ is not hydrogen.

6. A compound according to claim 1, in which $R^4$ is H and $R^1$ is —$CF_3$ or —COO($C_1$-$C_4$-alkyl).

7. A compound according to claim 1, in which $R^1$ and $R^4$ are H.

8. A compound of claim 7 selected from the group consisting of 2-n-octyloxynaphthacene-5,12-dione.

9. A compound according to claim 1, in which $R^5$ to $R^8$ are H and $R^1$ is unsubstituted $C_1$-$C_{12}$alkylthio, $C_1$-$C_2$alkoxy, phenyloxy, ($C_1$-$C_6$alkyl)phenyloxy or ($C_1$-$C_6$alkyl)phenylthio, or phenylthio or ($C_1$-$C_6$alkyl)phenylthio which is substituted by —F, —Cl, —OH, $C_1$-$C_4$alkoxy or $C_1$-$C_4$alkylthio.

10. A compound according to claim 1 in which one or both of $R^2$ and $R^3$ is $C_1$-$C_6$alkyl which is substituted by —CN or —COO($C_1$-$C_{12}$alkyl), or benzyl.

* * * * *